(12) United States Patent
Kawahara et al.

(10) Patent No.: US 9,861,640 B2
(45) Date of Patent: Jan. 9, 2018

(54) MEDICAMENT FOR TREATMENT OF ALZHEIMER'S DISEASE

(71) Applicant: KEMPHYS LTD., Tokyo (JP)

(72) Inventors: Kohichi Kawahara, Kumamoto (JP);
Michita Suenobu, Fukuoka (JP);
Koichi Shudo, Tokyo (JP)

(73) Assignee: KEMPHYS LTD., Tokyo (JP)

( * ) Notice: Subject to any disclaimer, the term of this patent is extended or adjusted under 35 U.S.C. 154(b) by 0 days.

(21) Appl. No.: 14/896,015

(22) PCT Filed: May 30, 2014

(86) PCT No.: PCT/JP2014/065025
§ 371 (c)(1),
(2) Date: Dec. 4, 2015

(87) PCT Pub. No.: WO2014/199905
PCT Pub. Date: Dec. 18, 2014

(65) Prior Publication Data
US 2016/0206624 A1    Jul. 21, 2016

Related U.S. Application Data

(60) Provisional application No. 61/833,040, filed on Jun. 10, 2013.

(51) Int. Cl.
| | | |
|---|---|---|
| *A61K 31/60* | (2006.01) | |
| *A61K 31/554* | (2006.01) | |
| *A61K 45/06* | (2006.01) | |
| *A61K 31/192* | (2006.01) | |
| *A61K 31/203* | (2006.01) | |
| *A61K 31/4418* | (2006.01) | |
| *A61K 31/55* | (2006.01) | |
| *A61K 31/616* | (2006.01) | |

(52) U.S. Cl.
CPC .......... *A61K 31/554* (2013.01); *A61K 31/192* (2013.01); *A61K 31/203* (2013.01); *A61K 31/4418* (2013.01); *A61K 45/06* (2013.01); *A61K 31/55* (2013.01); *A61K 31/616* (2013.01)

(58) Field of Classification Search
CPC .............................. A61K 31/55; A61K 31/616

USPC ............................................. 514/165, 211.09
See application file for complete search history.

(56) References Cited

U.S. PATENT DOCUMENTS

| | | | |
|---|---|---|---|
| 5,672,710 A * | 9/1997 | Beard | .................... C07C 317/44 544/239 |
| 6,063,797 A | 5/2000 | Fesus et al. | |
| 2012/0115912 A1 | 5/2012 | Landreth et al. | |

FOREIGN PATENT DOCUMENTS

| | | |
|---|---|---|
| JP | 11-500448 | 1/1999 |
| JP | 2012-532892 | 12/2012 |

OTHER PUBLICATIONS

Umemiya et al., "Action Mechanism of Retinoid-Synergistic Dibenzodiazepines", Biochemical and Biophysical Research Communications, vol. 233, No. 1, pp. 121-125 (1997).*
Fukasawa et al., "Tamibarontene: A Candidate Retinoid Drug for Alzheimer's Disease", Biological & Pharmaceutical Bulletin, vol. 35, No. 8, pp. 1206-1212 (2012).*
Shudo et al., "A Synthetic Retinoid Am80 (Tamibarotene) Rescues the Memory Deficit Caused by Scopolamine in a Passive Avoidance Paradigm," *Biol. Pharm. Bull.*, vol. 27, No. 11, pp. 1887-1889, 2004.
Fukasawa et al., "Tamibarotene: A Candidate Retinoid Drug for Alzheimer's Disease," *Biol. Pharm. Bull.*, vol. 35, No. 8, pp. 1206-1212, 2012.
Kawahara et al., "Oral Administration of Synthetic Retinoid Am80 (Tamibarotene) Decreases Brain β-Amyloid Peptides in APP23 Mice," *Biol. Pharm. Bull.*, vol. 32, No. 7, pp. 1307-1309, 2009.
Shudo, *Farumashia*, vol. 45, No. 12, pp. 1191-1194, 2009.
English translation of International Preliminary Report on Patentability issued in PCT/JP2014/065025, dated Dec. 23, 2015.
International Search Report issued in PCT/JP2014/065025, dated Aug. 19, 2014.
U.S. Appl. No. 61/833,040, filed Jun. 10, 2013.

* cited by examiner

*Primary Examiner* — Kevin E Weddington
(74) *Attorney, Agent, or Firm* — Greenblum & Bernstein, P.L.C.

(57) ABSTRACT

A medicament for therapeutic and/or preventive treatment of Alzheimer's disease, which comprises a combination of a retinoic acid receptor (RAR) agonist such as Am80 and a retinoid X receptor (RXR) agonist such as HX630.

4 Claims, 22 Drawing Sheets

[Fig. 1]
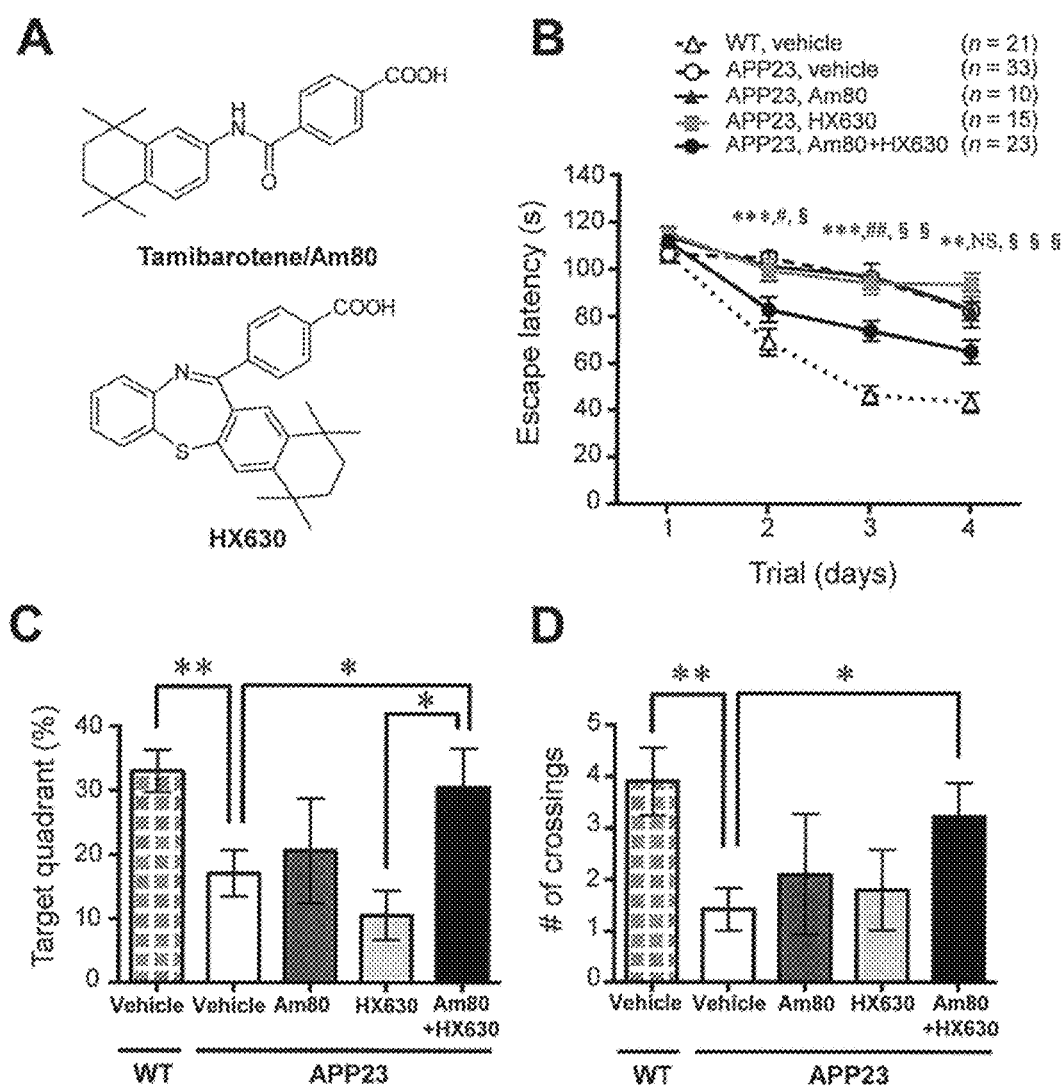

[Fig. 2]
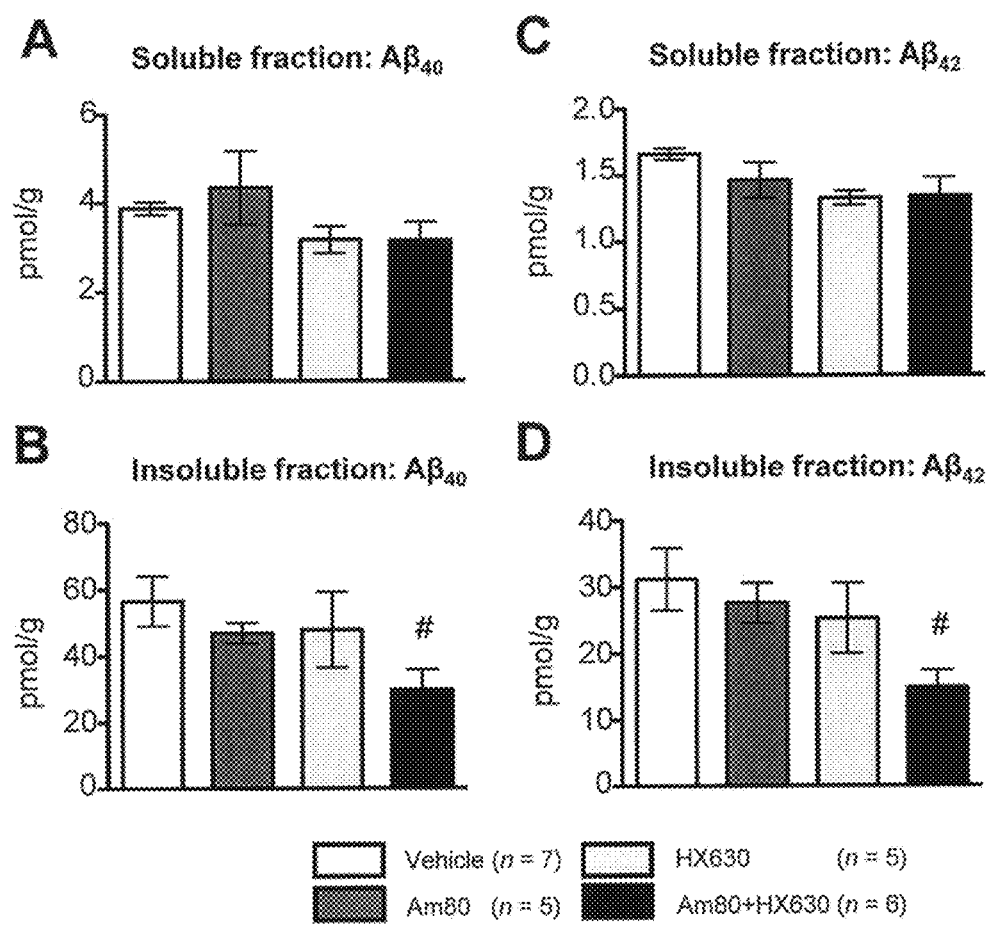

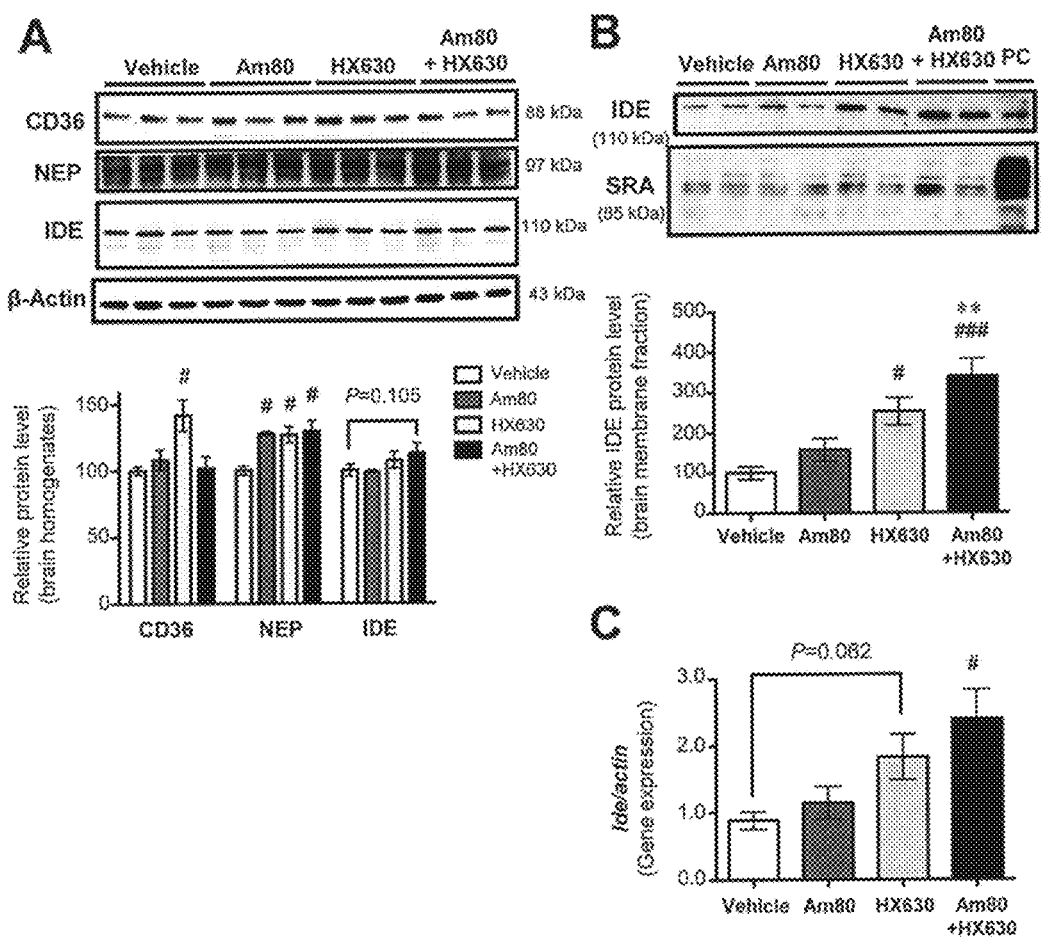
[Fig. 3]

[Fig. 4]
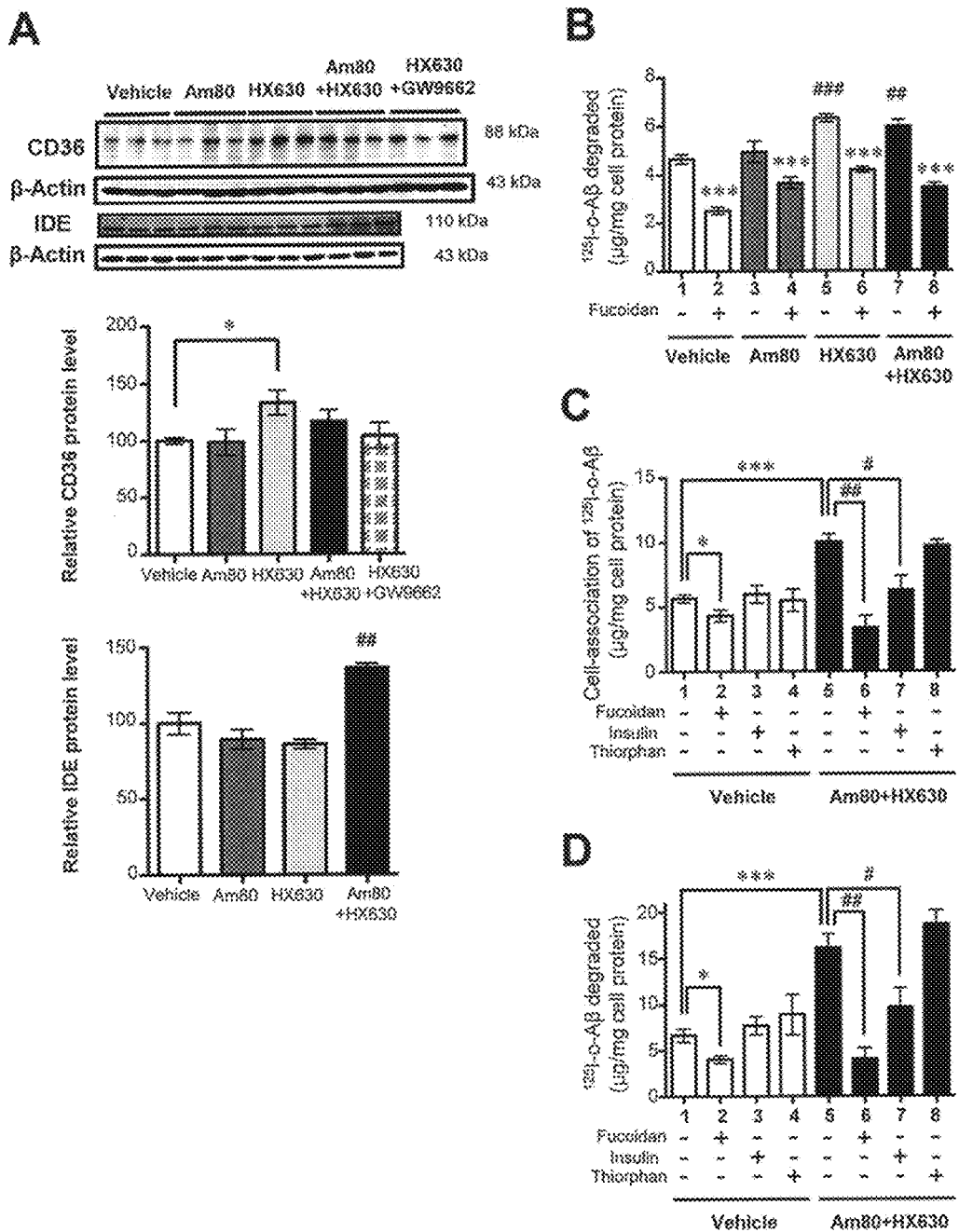

[Fig. 5]
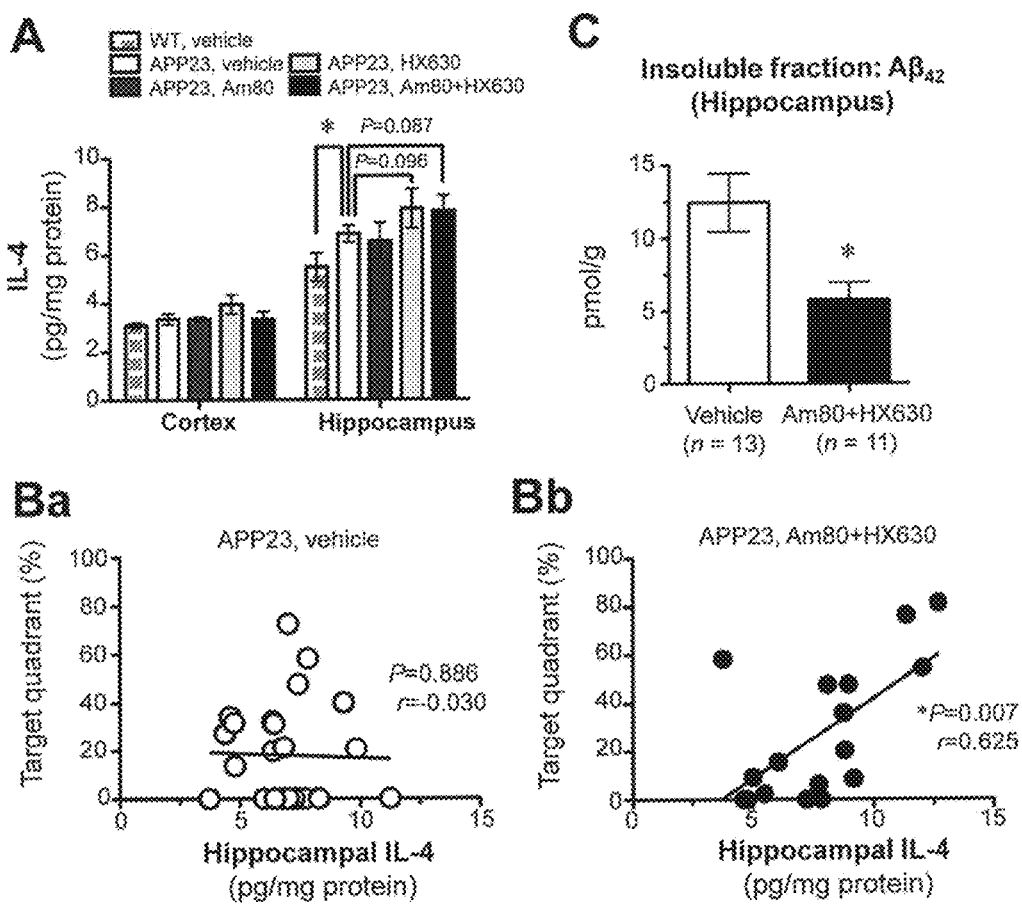

[Fig. 6]
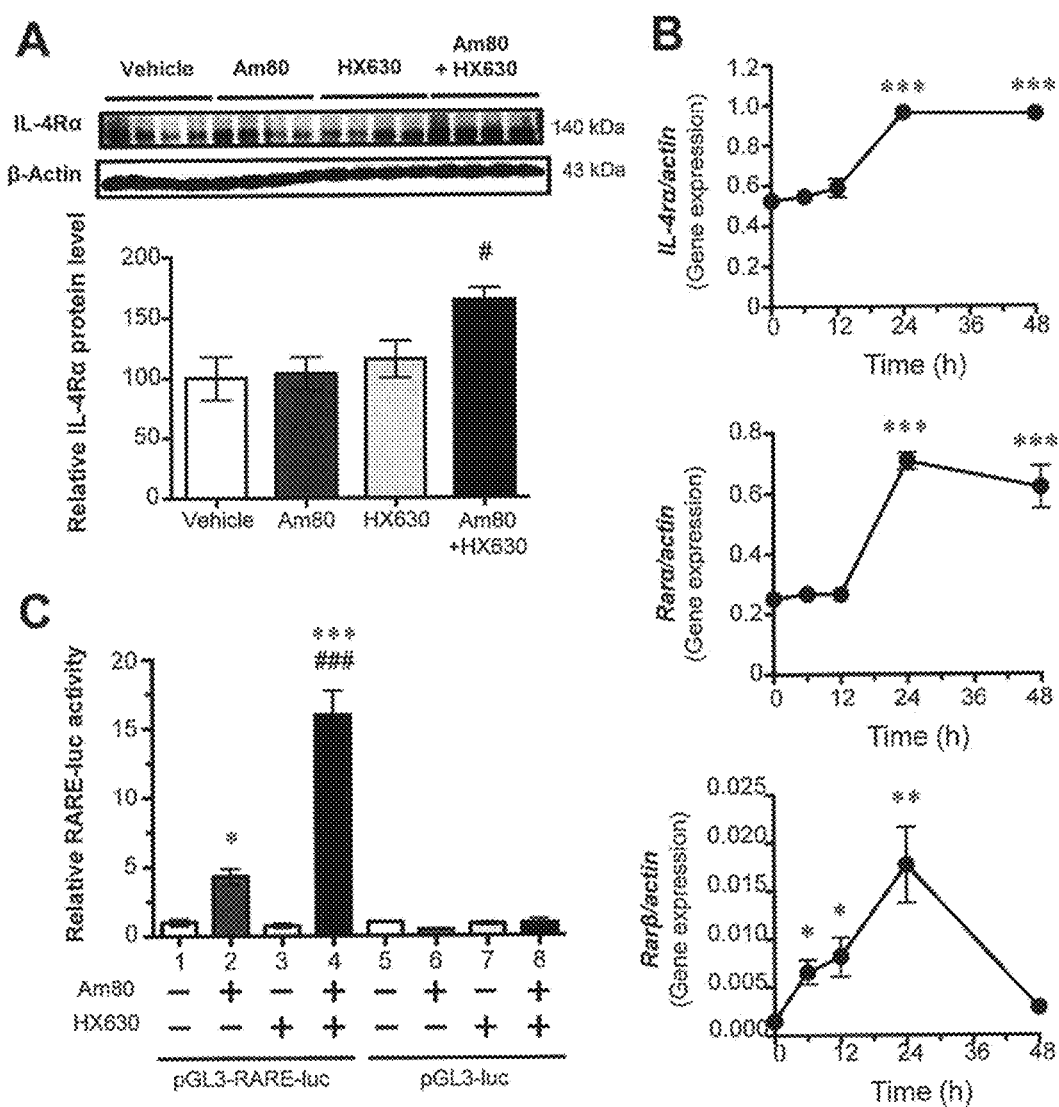

[Fig. 7]
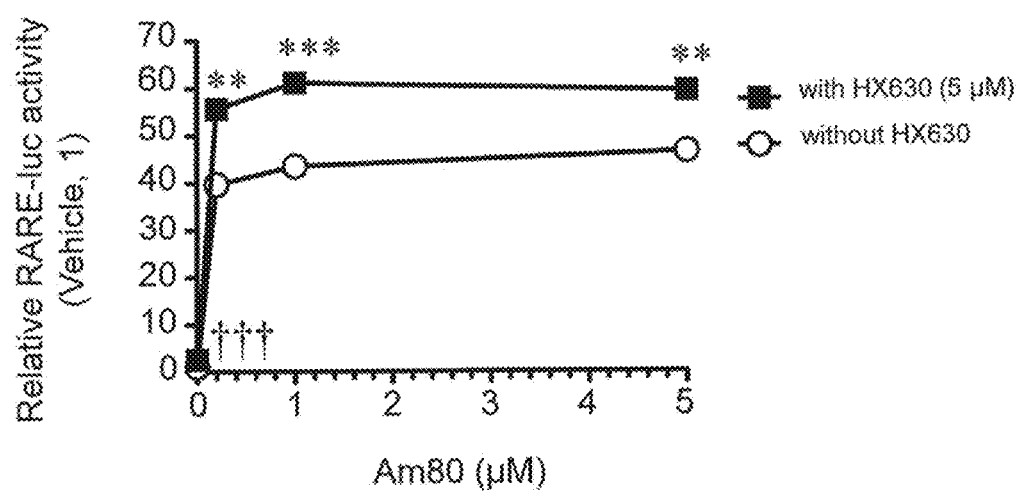

[Fig. 8]
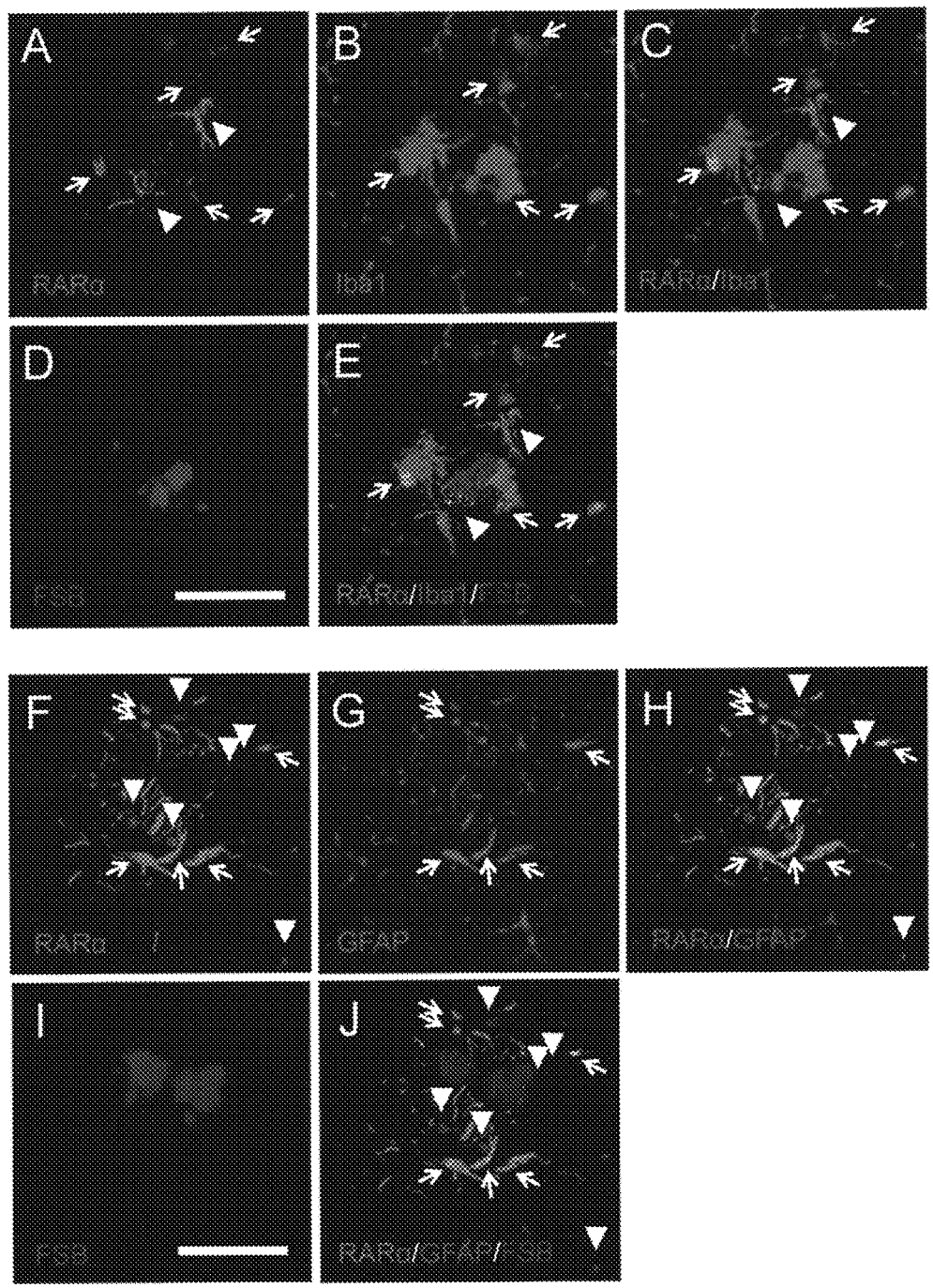

[Fig. 9]
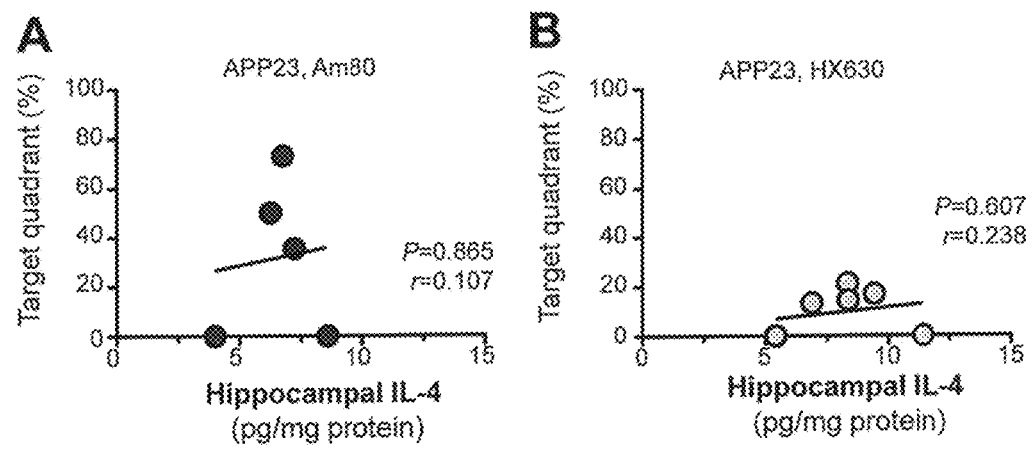

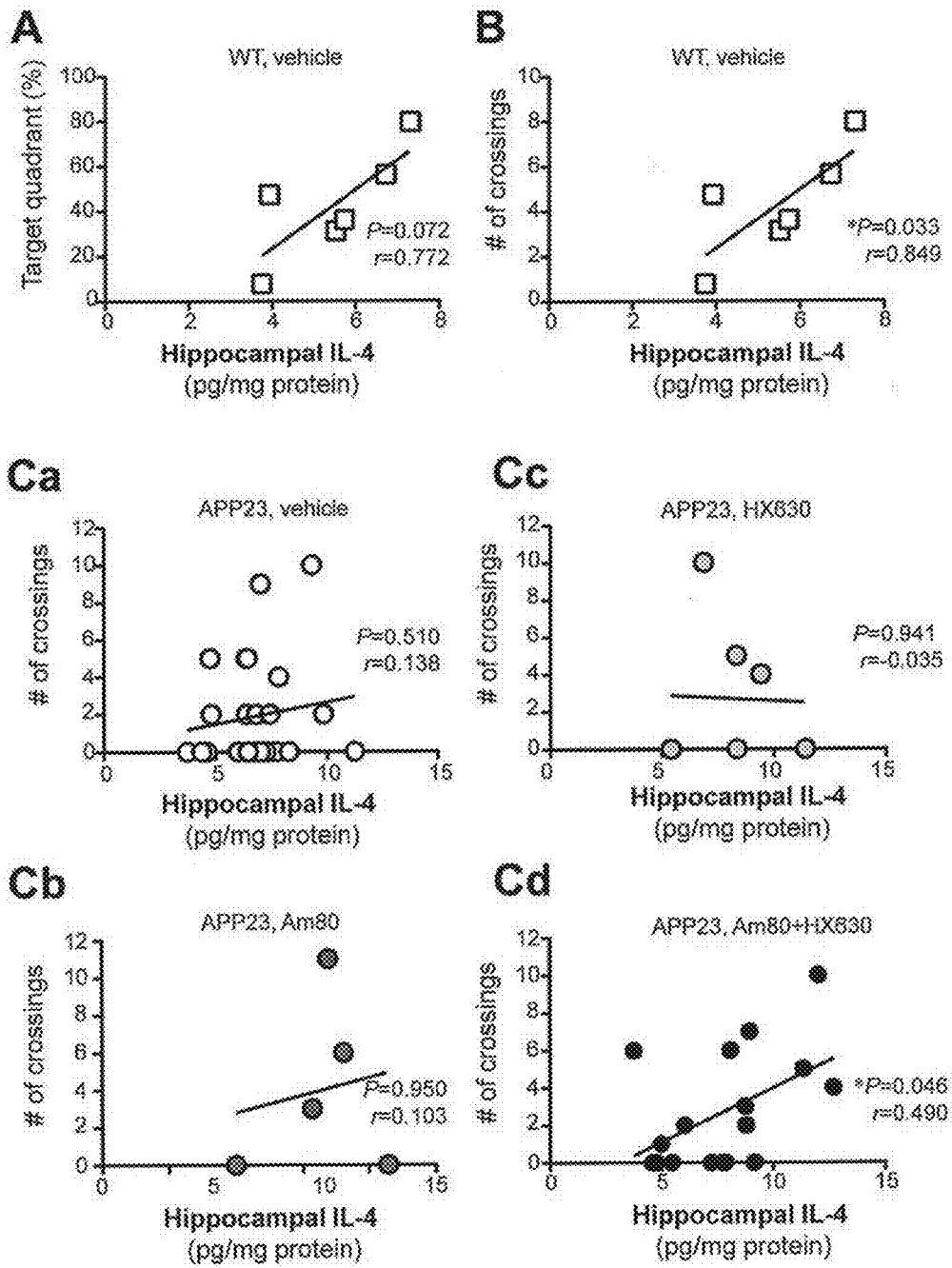
[Fig. 10]

[Fig. 11]
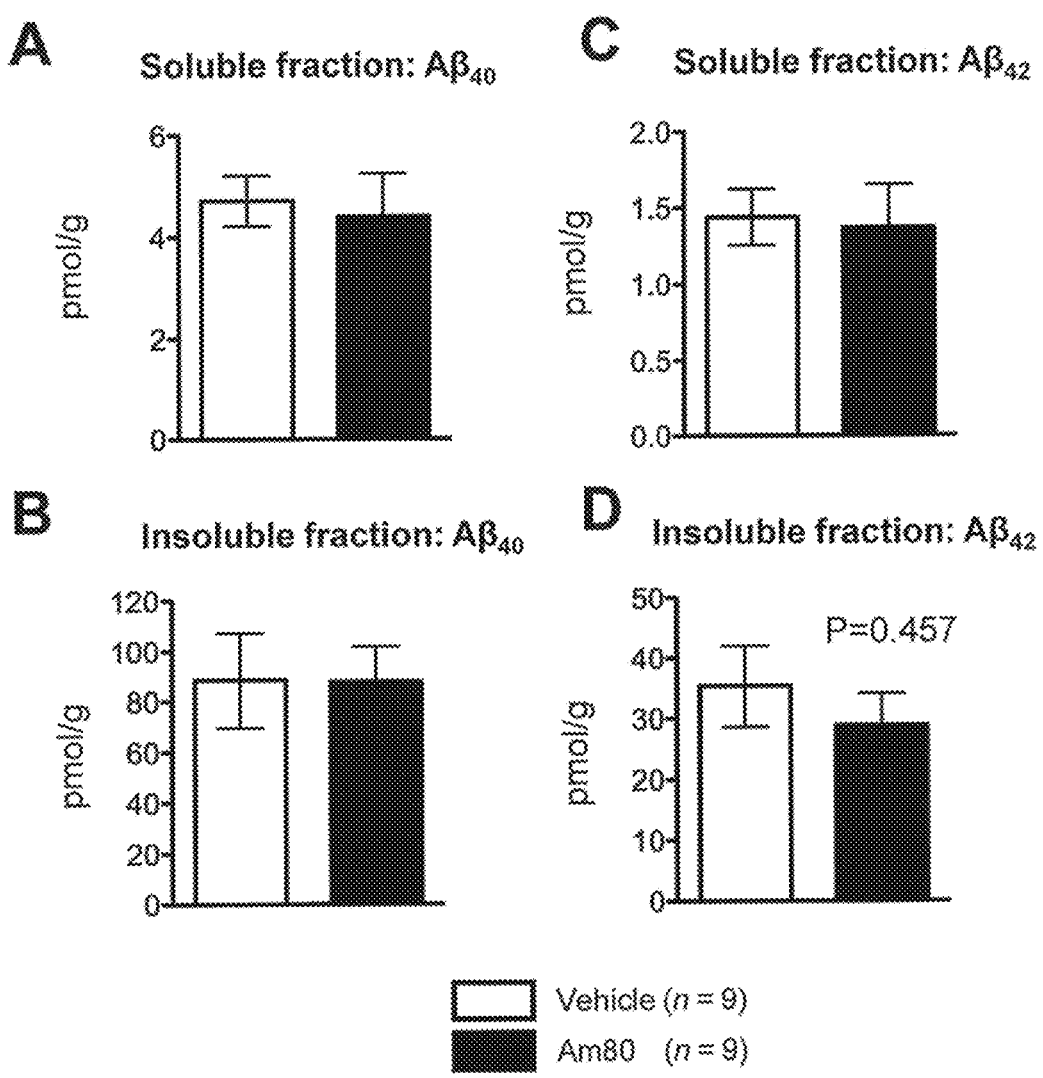

[Fig. 12]
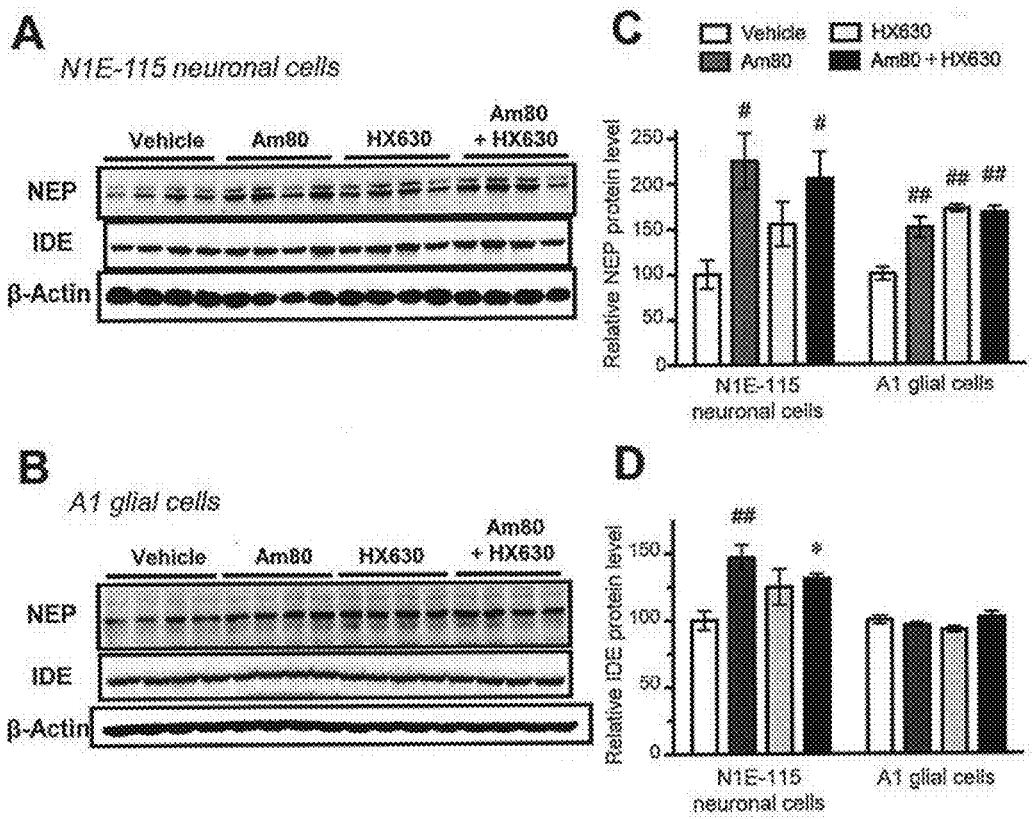

[Fig. 13]
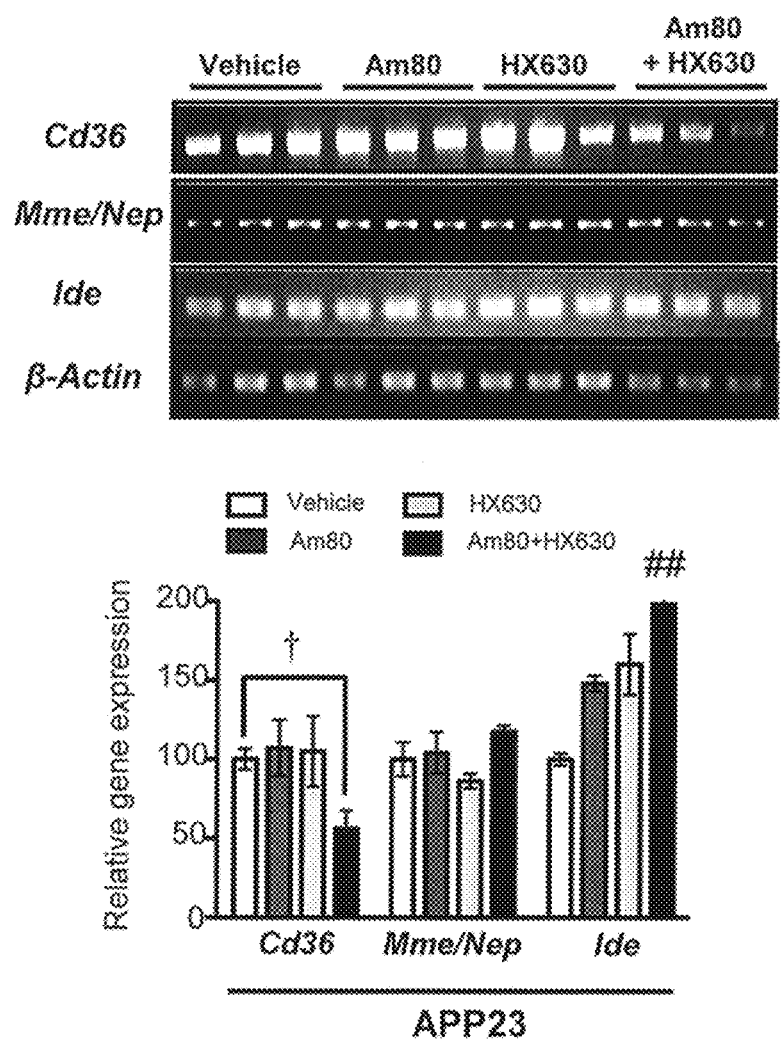

[Fig. 14]
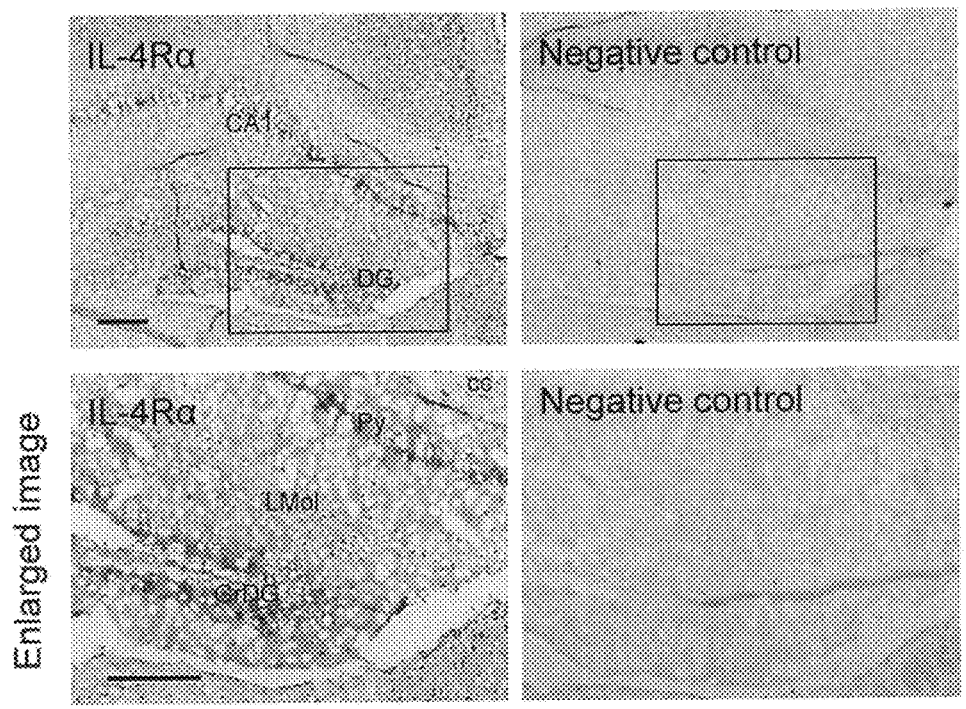
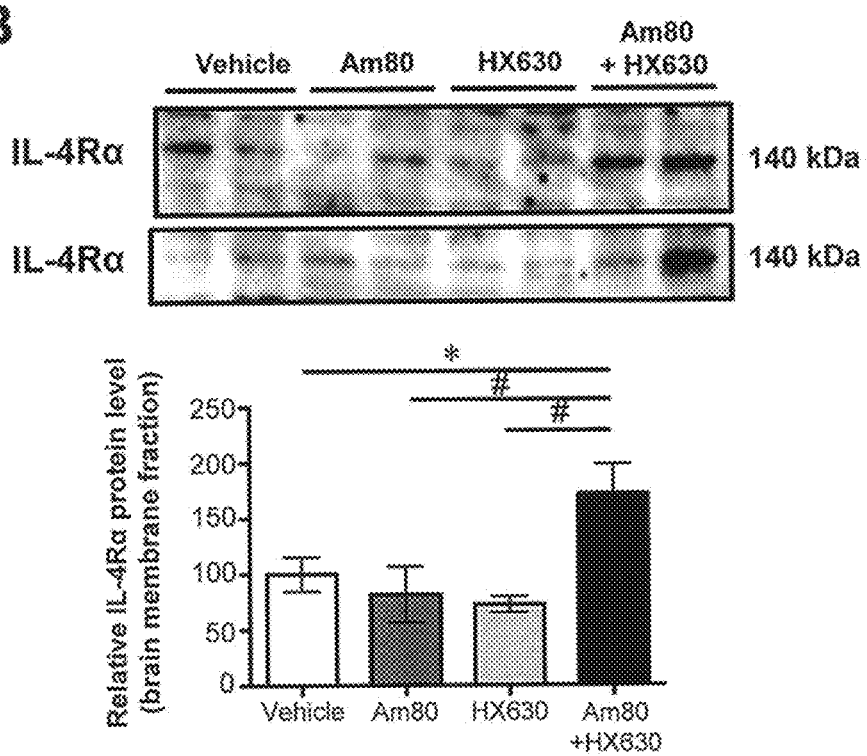

[Fig. 15]
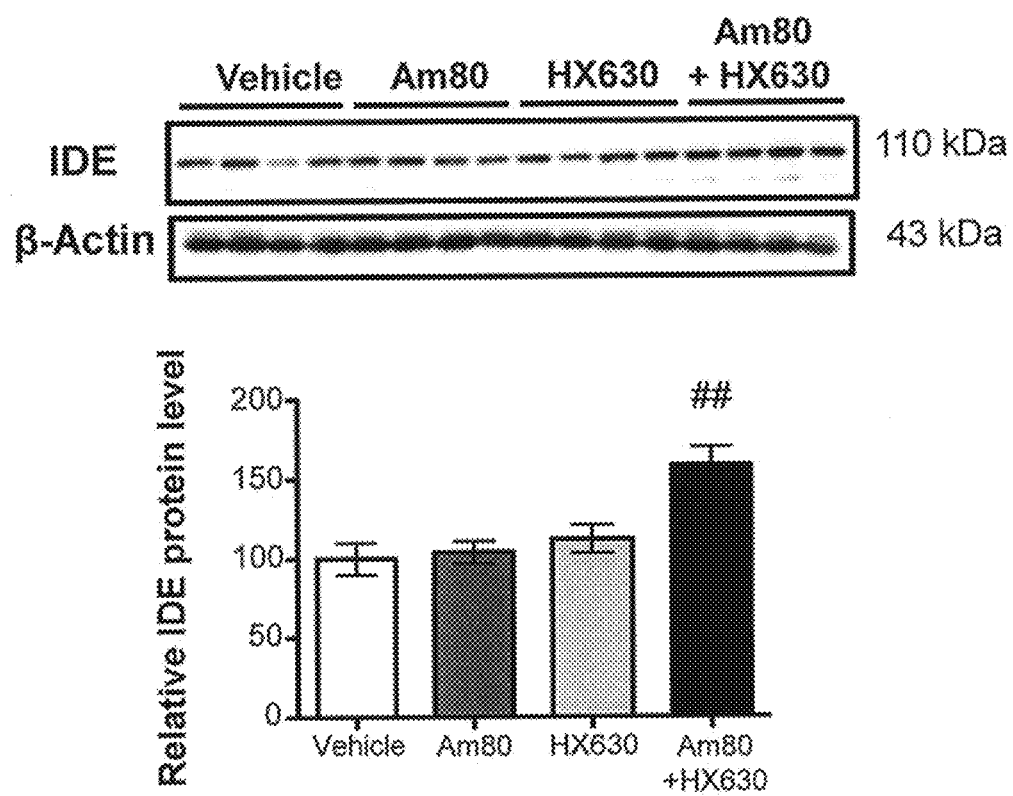

[Fig. 16]
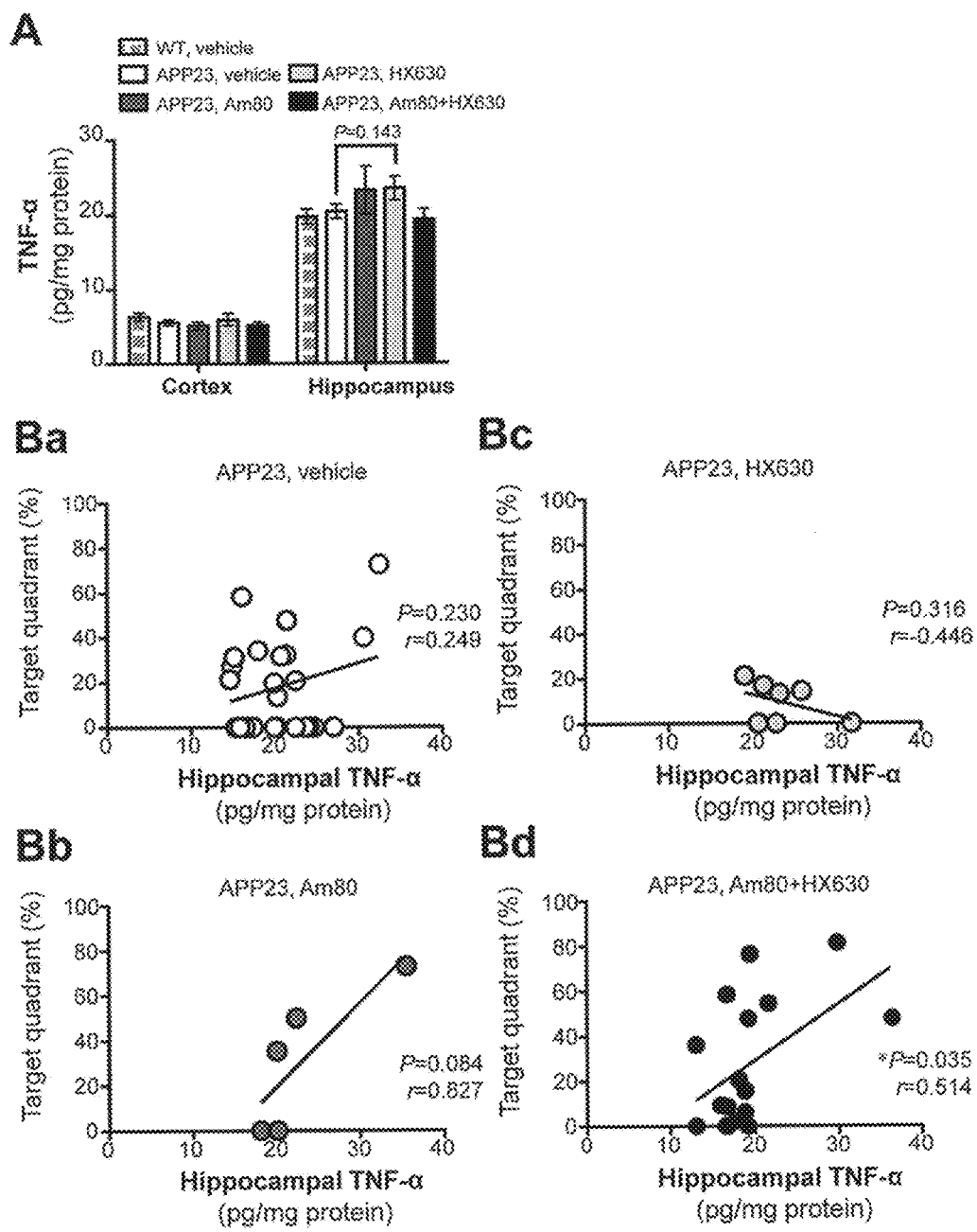

[Fig. 17]
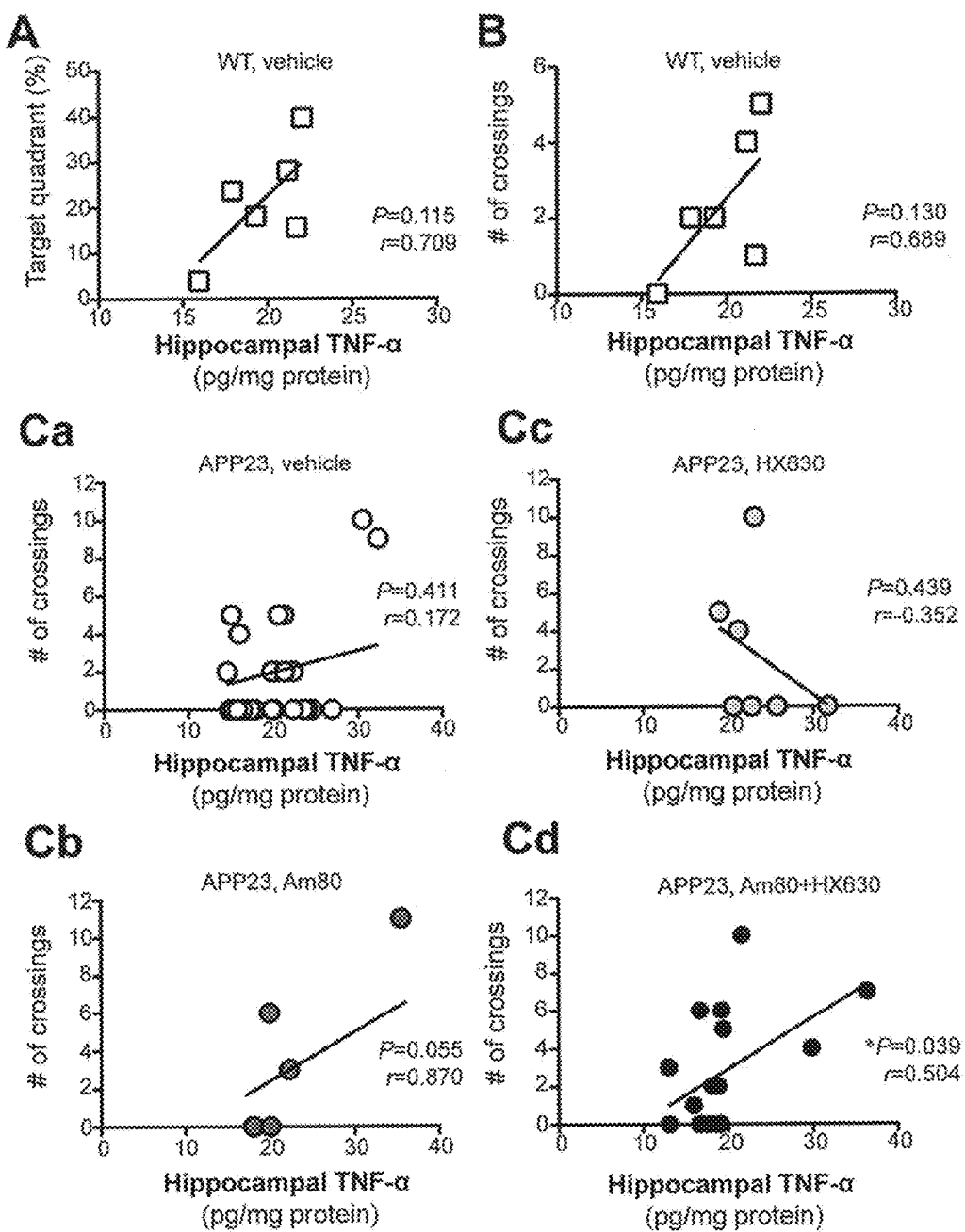

[Fig. 18]
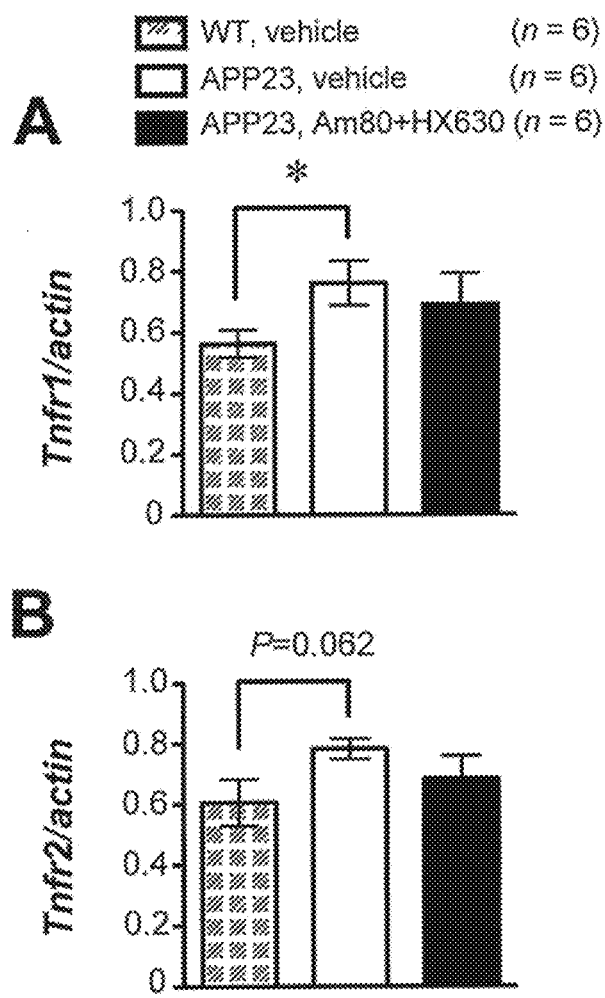

[Fig. 19]
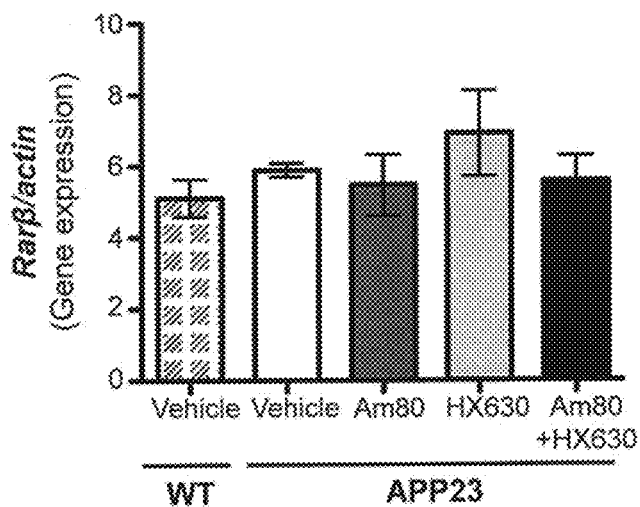
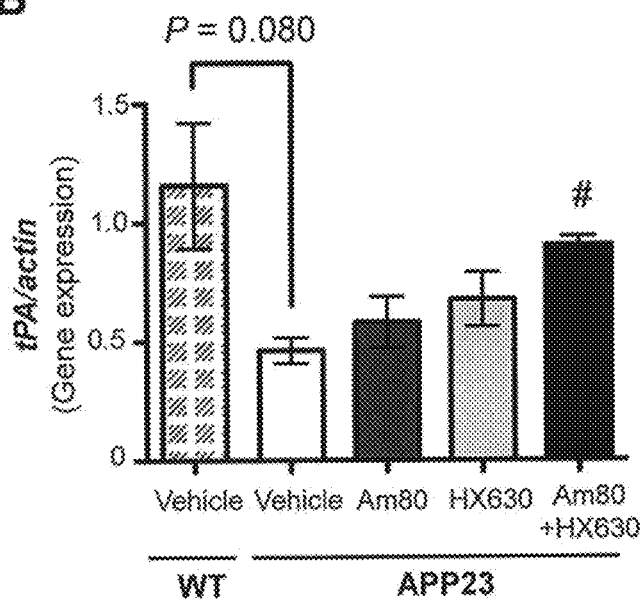

[Fig. 20]
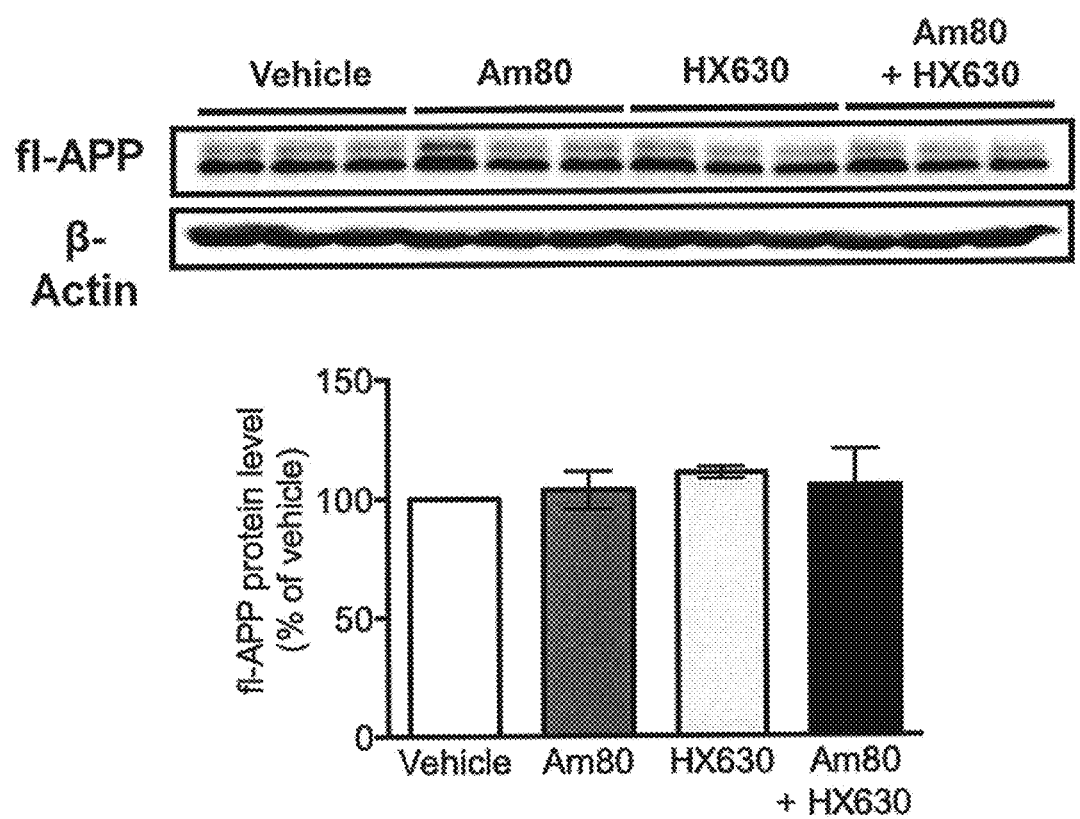

[Fig. 21]
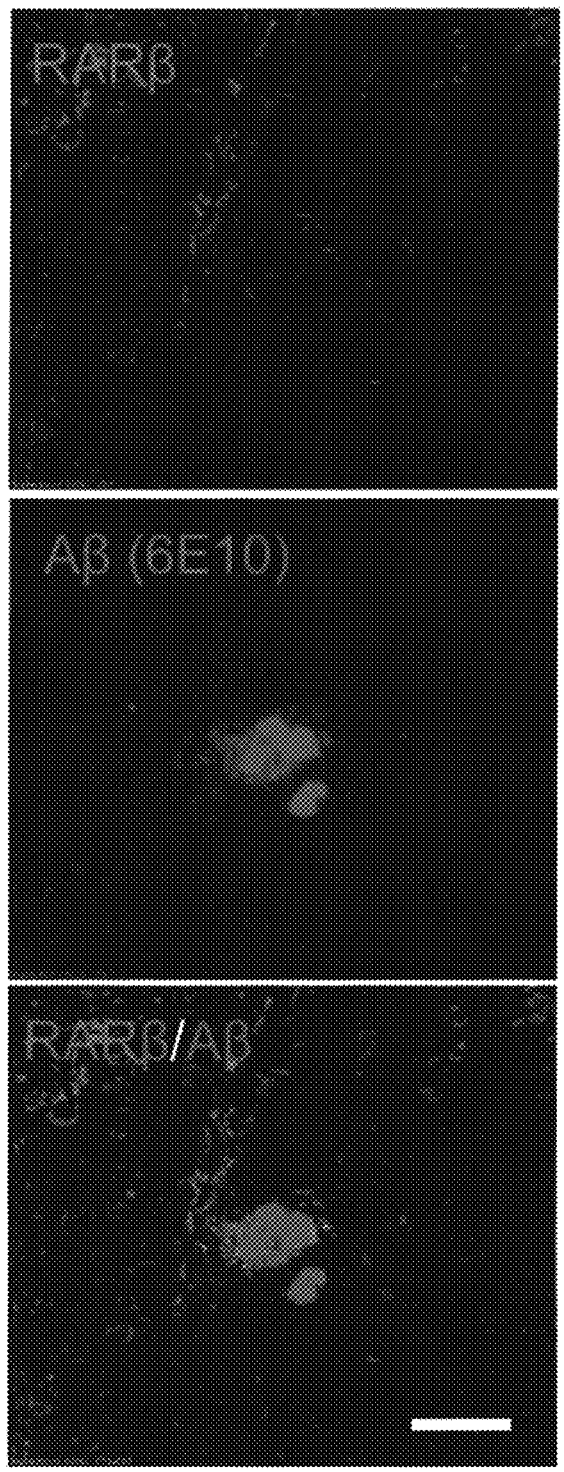

[Fig. 22]
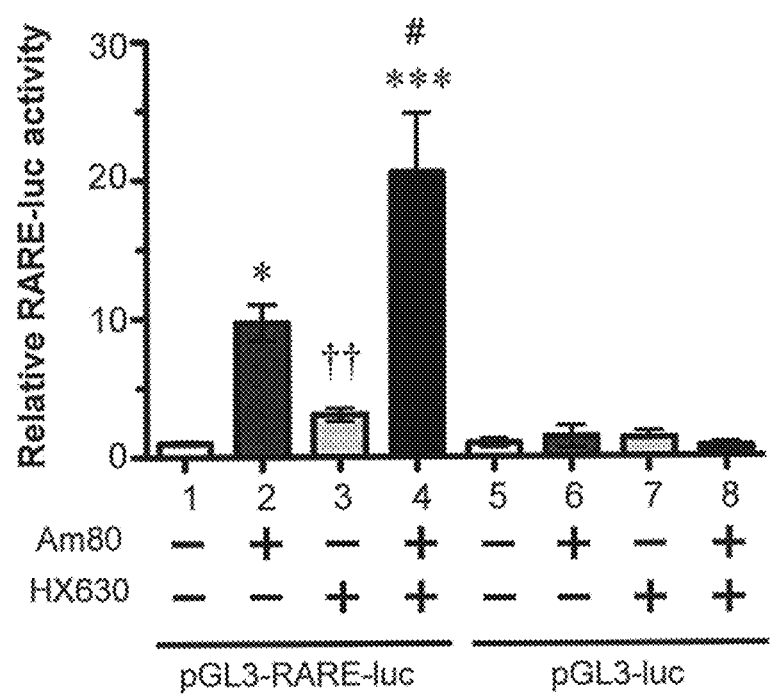

MEDICAMENT FOR TREATMENT OF ALZHEIMER'S DISEASE

CLAIM FOR PRIORITY

This application is a U.S. National Stage of PCT/W2014/065025 filed on May 30, 2014, and claims the priority benefit of U.S. provisional application 61/833,040, filed Jun. 10, 2013, the contents of which is expressly incorporated by reference herein in their entireties.

The instant application contains a Sequence Listing which has been submitted electronically in ASCII format and is hereby incorporated by reference in its entirety. Said ASCII copy, created on Mar. 2, 2016, is named P48840_SL.txt and is 5,962 bytes in size.

TECHNICAL FIELD

The present invention relates to a medicament for treatment of Alzheimer's disease.

BACKGROUND ART

Alzheimer's disease (AD) is a serious neurodegenerative disorder with no effective treatment. Its onset and progression correlate with neuroinflammatory processes [1], and inflammatory microglia are associated with AD-like pathology in a transgenic mouse model [2, 3].

Retinoids are analogues of vitamin A-derived all-trans retinoic acid (ATRA), and are specific modulators of many cellular functions, including immunity [4]. Retinoic acid (RA) exerts its biological actions by binding to its cognate nuclear receptors, retinoic acid receptors (RARs), which heterodimerize with retinoid X receptors (RXRs) to regulate transcription of target genes. Each of them has three subtypes: $RAR\alpha,\delta,\gamma$ and $RXR\alpha,\beta,\gamma$.

Vitamin A deprivation results in $A\beta$ accumulation in rats [5]. RA increases gene transcription of a disintegrin and metalloprotease, family 10 (ADAM10) [6-8] and increases its α-secretase activity, which cleaves a specific site of amyloid β-protein precursor (AβPP). This cleavage inhibits Aβ generation and leads to release of the soluble neuroprotective protein sAβPPα (9-11). Clinical evidence has indicated that late-onset AD brains have a defect in retinoid transport function [12]. Therefore, RA or synthetic retinoids may be candidates for treatment of AD [5, 13-17]. We previously demonstrated that oral administration of Am80 (0.5 mg/kg/d, for 14 weeks) reduced levels of Tris-buffered saline (TBS)-insoluble $A\beta_{42}$ in brains of 5-month-old APP23 mice, an AD model [15]. However, that study did not detect behavioral benefits of this treatment. Recently, Cramer et al. [16] reported that the RXR-selective agonist bexarotene enhanced apolipoprotein E-dependent Aα clearance from the brain and improved behavioral deficits in APP/PS1 mice. However, there are conflicting data regarding the therapeutic effect of bexarotene on AβPP mice [18-22]. Furthermore, it remains unclear whether co-activation of RARs with RXRs is required to improve AD pathology and memory deficits.

Retinoids modify T helper (Th) types 1 and 2 cells and regulatory T-cell-associated immune responses in rodents and humans [23]. They also suppress Th1 development and enhance development of naïve CD4 T cells to interleukin (IL)-4-producing Th2 cells [24]. IL-4 plays an essential role in higher functions, such as memory and learning, of normal brain [25]. For example, IL-4-deficient mice show cognitive impairment in spatial learning tasks [26]. However, it remains unclear whether retinoids affect AD-associated neuroinflammatory processes in vivo.

SUMMARY OF INVENTION

Technical Problem

The object of the present invention is to provide a medicament for effective treatment of Alzheimer's disease.

Solution to Problem

The inventor of the present invention investigated whether a combination of a retinoic acid receptor (RAR) agonist, such as Am80 as $RAR\alpha,\beta$ agonist [27, 28], and a retinoid X receptor (RXR) agonist, such as HX630 [29, 30], would produce any memory improvement in APP23 mice. The inventors also determined the brain levels of TBS-soluble and -insoluble Aβ and several molecules related to Aβ metabolism (including degradation and phagocytotic clearance of Aβ in vivo and in vitro) before and after the retinoid treatments. The inventors also examined the effects of Am80 and HX630 on neuroinflammatory processes in APP23 mice. As a result, the inventors found that the combination of RAR agonist such as Am80 and RXR pan agonist such as HX630 successfully achieved excellent memory improvement in APP23 mice and that the combination was effective for treatment of Alzheimer's disease. The present invention was achieved on the basis of these findings.

According to the present invention, provided is a medicament for therapeutic and/or preventive treatment of Alzheimer's disease, which comprises a combination of a retinoic acid receptor (RAR) agonist and a retinoid X receptor (RXR) agonist as an active ingredient.

From another aspect of the present invention, provided is a use of a retinoic acid receptor (RAR) agonist and/or a retinoid X receptor (RXR) agonist for manufacture of the medicament for therapeutic and/or preventive treatment of Alzheimer's disease which comprises a combination of a retinoic acid receptor (RAR) agonist and a retinoid X receptor (RXR) agonist as an active ingredient.

From further aspect of the present invention, provided are:

a method for therapeutic and/or preventive treatment of Alzheimer's disease, which comprises the step of administering to a mammal including human an effective amount of a combination of a retinoic acid receptor (RAR) agonist and a retinoid X receptor (RXR) agonist;

a method for therapeutic and/or preventive treatment of Alzheimer's disease, which comprises the step of co-activating RAR and RXR in a mammal including human;

a method for decreasing amyloid-β in a mammal including human by administering to the mammal an effective amount of a combination of a RAR agonist and a RXR agonist; and A method for enhancing expression of an amyloid-β degrading enzyme and/or α-secretase in a mammal including human by administering to the mammal an effective amount of a combination of a RAR agonist and a RXR agonist.

Advantageous Effects of Invention

The medicament of the present invention has an excellent activity of memory improvement, and therefore, the medicament of the present invention achieves effective therapeutic and/or preventive treatment of Alzheimer's disease.

BRIEF DESCRIPTION OF DRAWINGS

FIG. 1 Co-administration of Am80 with HX630 reversed deficits in spatial learning and memory in 8.5-month-old male APP23 mice. A, Chemical structure of synthetic retinoids, tamibarotene/Am80, and HX630. B-D, Am80 and/or HX630 were orally administered to mice at 0.5 mg/kg (Am80) or 5 mg/kg (HX630) for 17 consecutive days. Spatial learning and memory were evaluated by means of the MWM test from day 15 to day 18 of the first oral administration of the compounds. Error bare represent means±SEM (n=21 in vehicle-treated WT mice, n=33 in vehicle-treated APP23 mice, n=10 in Am80-treated APP23 mice, n=15 in HX630-treated APP23 mice, n=23 in Am80/HX630-treated APP23 mice). B, For 4 consecutive days, mice learned to swim to a hidden platform. Each point indicates the mean latency to find the escape platform in three to five trials per day± SEM for each group. Statistical significance of differences was calculated by using two-way ANOVA followed by the post hoc Bonferroni multiple comparison test. Significant differences with *$P<0.001$ (at days 2 and 3) and $P<0.01$ (at day 4) were detected between Am80/HX630-treated APP23 mice and vehicle-treated ones. Differences between Am80/HX630-treated APP23 mice and Am80-treated ones were observed as *$P<0.05$ (at day 2), $P<0.01$ (at day 3), and not significant (NS, at day 4) Significant differences between Am80/HX630-treated APP23 mice and HX630-treated ones were detected as §$P<0.05$ (at day 2), §§$P<0.01$ (at day 3), and §§§$P<0.001$ (at day 4). No significant difference was observed among the three groups: vehicle-treated, Am80-treated, and HX630-treated APP23 mice. C, D, Memory test in the MWM probe trial without the platform. The probe trial was administered at 2 h after the last training trial (i.e., at day 18 after the start of treatment). Measures included (C) the time (%) spent searching the target quadrant and (D) the number of crossings over the training annulus (3.1×the size of the target platform) during a probe trial (a 100-s session). $P<0.01$ and *$P<0.05$ by Student's t-test. No significant difference was observed for Am80/HX630 co-treatment relative to the Am80 (C, D) and HX630 treatments (D).

FIG. 2 Co-administration of Am80 (0.5 mg/kg/d) with HX630 (5 mg/kg/d) significantly reduced TBS-insoluble $A\beta_{40}$ and $A\beta_{42}$ levels in the brains of male APP23 mice. After the 4-day behavioral study (i.e., at 18 days after the start of treatment), $A\beta_{40}$ (A, B) and $A\beta_{42}$ (C, D) levels in TBS-soluble (A, C) and TBS-insoluble (B, D) fractions of mouse brains were determined by using sandwich ELISA. Error bars represent means±SEM. #$P<0.05$ by Dunnett's multiple comparison test, relative to the vehicle-treated groups. No significant difference was observed for the Am80/HX630 group compared to the Am80 and HX630 groups (B, D).

FIG. 3 Am80/HX630 increased NEP and IDE protein levels as well as Ide mRNA level in male APP23 mice. At 18 days after beginning treatment with Am80 (0.5 mg/kg/d) and/or HX630 (5 mg/kg/d), whole-cell extracts (A), homogenates of the membrane-bound fraction (B), and total RNA were prepared from the brains of APP23 mice (A-C). (A, B) Immunoblotting with antibodies to CD36, NEP, IDE, β-actin, or SRA was used to study the homogenates (40 µg in A, 5 µg in B). Positive controls (PC) in B are the membrane fractions (5 µg) from brains of WT mice for IDE, and cell lysates from MG5 microglial cells for SRA. The upper panel in B shows representative immunoblotting results of IDE and SRA in the membrane-bound fraction. Densitometric scanning was used to quantify results. Values were normalized to SRA protein expression, and were expressed relative to the vehicle-treated mice. Error bars represent means±SEM, n=3 (A) and 5 (B) mice per group. ###$P<0.001$ and #$P<0.05$ by Dunnett's multiple comparison test, relative to the vehicle-treated group. **$P<0.01$ by Dunnett's multiple comparison test, relative to the Am80-treated group. (C) The RNA samples (1.0 µg) were subjected to quantitative RT-PCR using a specific primer for Ide gene. Values were normalized to β-actin gene expression. Error bars represent means±SEM (n=3-4). #$P<0.05$ by Dunnett's multiple comparison test, relative to the vehicle-treated APP23 mice. $P=0.062$ by Student's t-test for HX630-treated APP23 mice, relative to the vehicle-treated APP23 mice.

FIG. 4 Clearance of $^{125}$I-labeled oligomeric $A\beta_{1-42}$ (o-$A\beta_{1-42}$) by rat primary microglia. A, Rat primary microglia were incubated with Am80 (5 µM) and/or HX630 (5 µM) for 48 h. Cell proteins (30 µg) were subjected to immunoblot analysis with antibodies to CD36, IDE, or β-actin. Densitometric scanning was used to quantify results. Values were normalized to β-actin protein expression, and were expressed relative to those of vehicle-treated cells. Error bars represent means±SEM (n=3). ##$P<0.01$ by Dunnett's multiple comparison test, relative to the vehicle-treated cells. B, Cells were cultured for 48 h with Am80 (5 µM) and/or HX630 (5 µM) and then incubated for 6 h with $^{125}$I-labeled o-$A\beta_{1-42}$ (1 µg/ml) in the presence or absence of fucoidan (100 µg/ml, a scavenger receptor inhibitor). The amounts of degradation products of $^{125}$I-labeled o-Aβ were determined. Error bars represent means±SEM, n=6. ###$P<0.001$ and ##$P<0.01$ by Dunnett's multiple comparison test, relative to the vehicle-treated cells (column 1). *$P<0.001$ by Student's t-test, in the presence or absence of fucoidan. C, D, Cells were cultured for 48 h with Am80 (5 µM) and/or HX630 (5 µM) and then incubated for 6 h with $^{125}$I-labeled o-$A\beta_{1-42}$ (1 µg/ml) in the presence or absence of fucoidan (100 µg/ml), insulin (100 µg/ml, an IDE inhibitor), or thiorphan (30 µM, a NEP inhibitor). The amounts of cell-association (C) and degradation products (D) of $^{125}$I-labeled o-Aβ were determined. Error bars represent means±SEM, n=6. *$P<0.001$ and *$P<0.05$ by Student's t-test. ##$P<0.01$ and #$P<0.05$ for column 5 among columns 5-8, by Dunnett's multiple comparison test.

FIG. 5 Am80/HX630-treated male APP23 mice showed a significant positive correlation between hippocampal IL-4 levels and performance in the MWM test, but vehicle-treated mice did not. A, At 18 days after beginning treatment with Am80 (0.5 mg/kg/d) and/or HX630 (5 mg/kg/d), levels of IL-4 in TBS-soluble fractions of the cerebral cortex and hippocampus were determined via sandwich ELISA. Error bars represent means±SEM (n=6 in vehicle-treated WT mice, n=25 in vehicle-treated APP23 mice, n=5 in Am80-treated APP23 mice, n=7 in HX630-treated APP23 mice, n=17 in Am80/HX630-treated APP23 mice). B, Scatterplot and Pearson correlation analyses were used to determine the relationship between IL-4 values in the hippocampus and the percent time spent in the target quadrant, for vehicle- (Ba), and Am80/HX630-treated APP23 mice (Bb). C, At 18 days after beginning treatment with Am80 (0.5 mg/mg/d) and HX630 (5 mg/kg/d), levels of $A\beta_{42}$ in TBS-insoluble fractions of the hippocampus were determined via sandwich ELISA. *$P<0.05$ by Student's t-test.

FIG. 6 Am80 with HX630 synergistically increased IL-4Rα protein and RARE reporter activity in mouse microglial MG5 cells, A, MG5 cells were incubated for 48 h with Am80 (5 µM) and/or HX630 (5 µM). Cell proteins (30 µg) were subjected to immunoblot analysis with antibodies to IL-4Rα and β-actin. Densitometric scanning was used to quantify results. Values were normalized to β.actin expression and expressed relative to the vehicle-treated cells. Error bars represent means±SEM (n=4). #P<0.05 by Dunnett's multiple comparison test, relative to the vehicle-treated cells. B, RNA from MG5 cells treated with Am80 (5 µM) plus HX630 (5 µM) for indicated periods was subjected to quantitative RT-PCR with specific primers for I1-4rα, Rarα, Rarβ, and β-actin genes. Total RNA from mouse liver was used as the calibrator sample for I1-4rα, Rarα, Rarβ, and β-actin genes. Values were normalized to β-actin gene expression. Error bars represent means±SEM (n=4). *P<0.001, P<0.01, and *P<0.05 by Student's t-test, relative to the untreated cells. C, Cells were transfected with the pGL3-RARE-Luc or pGL3-Luc reporter plasmid together with a phRL-TK internal control and were treated with Am80 (5 µM) and/or HX630 (5 µM). Luciferase activity in the cell extract was normalized to Renilla luciferase activity and was expressed as fold induction relative to the vehicle-treated cells. Error bars represent means±SEM (n=4). ***P<0.001 and *P<0.05 by Dunnett's multiple comparison test, relative to the vehicle-treated cells (column 1). ###P<0.001 by Dunnett's multiple comparison test, relative to the Am80-treated cells (column 2).

FIG. 7 Supplementary FIG. 1. Am80 with HX630 synergistically increased RARE reporter activity in mouse Neuro2a cells in the concentration of 0.2-5 µM Am80 and 5 µM HX630. Cells were transfected with the pGL3-RARE-Luc or pGL3-Luc reporter plasmid together with a phRL-TK internal control and were treated with or without HX630 (5 µM) in the presence of absence of indicated concentration of Am80 (0, 0.2, 1, 5 µM) for 24 h. Luciferase activity in the cell extract was normalized to Renilla luciferase activity and was expressed as fold induction relative to the vehicle-treated cells. Error bars represent means±SEM (n=3). *P<0.001 and P<0.01 by Dunnett's test, between HX630-treated cells and Am80/HX630-treated cells and in each concentration of Am80. †††P<0.001 by Dunnett's test, between HX630-treated cells and vehicle-treated cells.

FIG. 8 Supplementary FIG. 2. RARα was expressed in microglia and astrocytes present in the vicinity of amyloid plaques. (A-E) Triple staining with anti-RARα antibody (A, green), anti-Iba1 antibody (Iba1 is a microglial marker)(B, red), and FSB (FSB is a probe for amyloid plaque)(D, blue) in brain of a vehicle-treated 8.5-month-old male APP23 mouse. Two-channel images (A and B) are shown in C. Three-channel images (A, B, and D) are shown in E. The arrows indicate RARα$^+$Iba1$^+$ cells. The arrowheads indicate RARα$^+$Iba1$^{30}$ cells. (F-J) Triple staining with anti-RARα antibody (F, green), anti-GFAP antibody (GFAP is an astrocyte marker)(G, red), and FSB (I, blue) in brain of a vehicle-treated 8.5-month-old male APP23 mouse. Two-channel images (F and G) are shown in H. Three-channel images (F, G, and I) are shown in J. The arrows indicate RARα$^+$GFAP$^+$ cells. The arrowheads indicate RARα$^+$ GFAP$^+$ cells. Scale bar, 40 µm.

FIG. 9 Supplementary FIG. 3. 8.5-month-old male APP23 mice treated with a single retinoid alone (Am80 or HX630) did not show a significant positive correlation between hippocampal IL-4 levels and performance in the MWM test. At 18 days after beginning treatment with Am80 (0.5 mg/kg/d) or HX630 (5 mg/kg/d), levels of IL-4 in TBS-soluble fractions of the hippocampus were determined via sandwich ELISA (n=5 in Am80-treated APP23 mice, n=7 in HX630-treated APP23 mice). Scatterplot and Pearson correlation analyses were used to determine the relationship between IL-4 values in the hippocampus and the percent time spent in the target quadrant, for Am80-(A), and HX630-treated APP23 mice (B).

FIG. 10 Supplementary FIG. 4. The relationship between IL-4 values in the hippocampus and performance in MWM test in the mice. A, Scatterplot and Pearson correlation analyses were used to determine the relationship between IL-4 values in the hippocampus and the percent time spent in the target quadrant, for vehicle-treated WT mice. B, C, The relationship between IL-4 values in the hippocampus and the number of crossings over the target annulus during a probe trial, for vehicle-treated WT mice (B), and for vehicle-(Ca), Am80-(Cb), HX630-(Cc), and Am80/HX630-treated APP23 mice (Cd). n=6 for vehicle-treated WT mice, n=25 for vehicle-treated APP23 mice, n=5 for Am80-treated APP23 mice, n=7 for HX630-treated APP23 mice, n=17 for Am80/HX630-treated APP23 mice.

FIG. 11 Supplementary FIG. 5. A higher dose of Am80 (3 mg/kg/d) had no effect on Aβlevels in brains of 8.5-month-old male APP23 mice. Am80 was orally administered to mice at 3 mg/kg for 17 consecutive days. At 18 days after the start of treatment, $Aβ_{40}$ (A, B) and $Aβ_{42}$ (C, D) levels in TBS-soluble (A, C) and TBS-insoluble (B, D) fractions of mouse brains were determined by using sandwich ELISA. Error bars represent means±SEM (n=9). P=0.457 by Student's t-test, between Am80 and vehicle groups.

FIG. 12 Supplementary FIG. 6. Am80/HX630 increased levels of NEP and IDE proteins in neuronal and glial cells. Mouse neuronal N1E-116 cells (A), and mouse A1 glial cells (B) were incubated for 5 days (A) or 2 days (B) with Am80 (5 µM) and/or HX630 (5 µM). Cell proteins (30 µg) were subjected to immunoblot analysis with antibodies to NEP, IDE, or β-actin. (C, D) Densitometric scanning was used to quantify results in A, B, with values normalized to β-actin expression and expressed relative to the vehicle-treated cells. Values are means±SEM (n=4). ##P<0.01 and #P<0.05 by Dunnett's multiple comparison test, relative to the vehicle-treated cells. *P<0.05 by Student's t-test, relative to the vehicle-treated cells.

FIG. 13 Supplementary FIG. 7. Am80/HX630 increased Ide mRNA and decreased Cd36 mRNA in 8.5 month-old male APP23 mice. At 18 days after beginning treatment with Am80 (0.5 mg/kg/d) and/or HX630 (5 mg/kg/d), total RNA was prepared from brains of APP23 mice. Total RNA (1.0 µg) was subjected to semi-quantitative RT-PCR with a specific primer for each gene. Densitometric scanning was used to quantify results, with values normalized to β-actin gene expression and expressed relative to the vehicle-treated APP23 mice. Error bars represent means±SEM (n=3). #P<0.05 by Dunnett's multiple comparison test, relative to the vehicle-treated group. †P<0.05 by Student's t-test, relative to the vehicle-treated group.

FIG. 14 Supplementary FIG. 8. Am80/HX630 increased the IL-4Rα protein level in male APP23 mice. (A) Light microscopic images of IL-4Rα-immunoreactivity shown in the hippocampus of 8.5-month-old APP23 mice. Lower panel: higher magnification image of IL-4Rα staining. CA1: field CA1 of the hippocampus; DG: dentate gyrus; cc: corpus callosum; Py: pyramidal cell layer of the hippocampus; GrDG: granule cell layer of the dentate gyrus; LMol; lacunosum moleculare layer of the hippocampus. Scale bar, 50 µm. (B) At 18 days after beginning treatment with Am80 (0.5 mg/kg/d) and/or HX630 (5 mg/kg/d), homogenates of the membrane-bound fraction were prepared from the whole brains of APP23 mice. Immunoblotting with antibodies to IL-4Rα was used to study the homogenates (5 µg/lane).

Densitometric scanning was used to quantify results. Values were expressed relative to the vehicle-treated mice. Error bars represent means±SEM, n=4 mice per group. #P<0.05 by Dunnett's multiple comparison test, relative to the Am80/HX630-treated group. *P<0.05 by Student's t-test for Am80/HX630-treated APP23 mice, relative to the vehicle-treated APP23 mice.

FIG. 15 Supplementary FIG. 9. Am80/HX630 increased levels of IDE proteins in mouse microglial MG5 cells. Mouse microglial MG5 cells were incubated for 48 h with Am80 (5 μM) and/or HX630 (5 μM). Cell proteins (30 μg) were subjected to immunoblot analysis with antibodies to IDE, or β-actin. The IDE values were normalized to β-actin expression and expressed relative to the vehicle-treated cells. Values are means±SEM (n=4). ##P<0.01 by Dunnett's multiple comparison test, relative to the vehicle-treated cells.

FIG. 16 Supplementary FIG. 10. Am80/HX630-treated male APP23 mice showed a significant positive correlation between hippocampal TNF-α levels and performance in the MWM test, but vehicle-treated mice did not. A, At 18 days after beginning treatment with Am80 (0.5 mg/kg/d) and/or HX630 (5 mg/kg/d), levels of TNF-α in TBS-soluble fractions of the cerebral cortex and hippocampus were determined by means of sandwich ELISA. Error bare represent means±SEM (n=6 for vehicle-treated WT mice, n=25 for vehicle-treated APP23 mice, n=5 for Am80-treated APP23 mice, n=7 for HX630-treated APP23 mice, n=17 for Am80/HX630-treated APP23 mice). B, Scatterplot and Pearson correlation analyses were used to determine the relationship between TNF-α values in the hippocampus and the percent time spent in the target quadrant, for the vehicle-(Ba), Am80- (Bb), HX630- (Bc), and Am80/HX630-treated APP23 mice (Bd).

FIG. 17 Supplementary FIG. 11. The relationship between TNF-α values in the hippocampus and performance in the MWM test. A, Scatterplot and Pearson correlation analyses were used to determine the relationship between TNF-α values in the hippocampus and the percent time spent in the target quadrant for vehicle-treated WT mice. B, C, The relationship between TNF-α values in the hippocampus and the number of crossings over the target annulus for vehicle-treated WIT mice (B), and for vehicle-(Ca), Am80-(Cb), HX630-(Cc), and Am80/HX630-treated APP23 mice (Cd). n=6 for vehicle-treated WT mice, n=25 for vehicle-treated APP23 mice, n=5 for Am80-treated APP23 mice, n=7 for HX630-treated APP23 mice, n=17 for Am80/HX630-treated APP23 mice.

FIG. 18 Supplementary FIG. 12. Hippocampal Tnfr1 mRNA level in APP23 mice is higher than that in WT mice. At 18 days after beginning treatment with Am80 (0.5 mg/kg/d) and HX630 (5 mg/kg/d), total RNA was prepared from hippocampus of APP23 mice or WT mice. RNA samples were subjected to quantitative RT-PCR using a specific primer for each gene (A: Tnfr1; B: Tnfr2). Values were normalized to β-actin gene expression. Error bars represent means±SEM (n=6). *P<0.05 by Student's t-test.

FIG. 19 Supplementary FIG. 13. Am80/HX630 increased the tPA mRNA level in male APP23 mice. At 18 days after beginning treatment with Am80 (0.5 mg/kg/d) and/or HX630 (5 mg/kg/d), total RNA was prepared from the brains of APP23 mice or WT mice. The RNA samples (1.0 μg) were subjected to quantitative RT-PCR using specific primers for Rarβ and tPA genes. Values were normalized to β-actin gene expression. Error bars represent means±SEM (n=3-4). #P<0.05 by Dunnett's multiple comparison test, relative to the vehicle-treated APP23 mice. P=0.080 by Student's t-test, between vehicle-treated WT mice and APP23 mice.

FIG. 20 Supplementary FIG. 14. Am80, HX630, and their combination had no effect on the total amount of full-length (fl)-APP in 8.5-month-old male APP23 mice. At 18 days after beginning treatment of APP23 mice with Am80 (0.5 mg/kg/d) and/or HX630 (5 mg/kg/d), whole-cell extracts were prepared from their brains. (A) These extracts (30 μg) were subjected to immunoblotting with the antibody to APP (6E10) or β-actin. Densitometric scanning was used to determine the band intensities of full-length (fl)-APP. Values were normalized to β-actin and were expressed relative to those for vehicle-treated mice. Error bars represent means±SEM (n=3). No significant difference was observed among the four groups.

FIG. 21 Supplementary FIG. 15. RARβ was uniformly expressed in the vicinity of amyloid plaques. Images show double staining with anti-RARβ antibody (green) and anti-Aβ antibody (6E10, red) in brain of a vehicle-treated 8.5-month-old male APP23 mouse. Scale bar, 50 μm.

FIG. 22 Supplementary FIG. 16. Am80 with HX630 synergistically increased RARE reporter activity in mouse microglial MG5 cells. MG5 cells were transfected with the pGL3-RARE-Luc or pGL3-Luc reporter plasmid together with a phRL-TK internal control in the presence of pcDNA3.1-RAR and pcDNA3.1-RXR plasmids, and were treated with Am80 (5 μM) and/or HX630 (5 μM). Luciferase activity in the cell extract was normalized to Renilla luciferase activity and was expressed as fold induction relative to the vehicle-treated cells. Error bars represent means±SEM (n=4). ***P<0.001 and *P<0.05 by Dunnett's multiple comparison test, relative to the vehicle-treated cells (column 1). #P<0.05 by Dunnett's multiple comparison test, relative to the Am80-treated cells (column 2). ††P<0.01 by Student's t-test, between the vehicle-treated cells (column 1) and the HX630-treated cells (column 3).

DESCRIPTION OF EMBODIMENTS

According to the present invention, the RAR agonist can be chosen, for example, from the group consisting of all trans retinoic acid (ATRA), 4-{(5,6,7,8-tetrahydro-5,5,8,8-tetramethyl-2-naphthalenyl)carbamoyl}benzoic acid (Am80), 4-{(5,6,7,8-tetrahydro5,5,8,8-tetramethyl-2-naphthalenyl)carboxamido}benzoic acid (Am580), 4-{(3,5-bistrimethylsilylphenyl)carbamoyl}benzoic acid (Tac101), 4-[(5,6,7,7a,8,9,10,11-octahydro-4H-2-benzo[ef]heptalenyl)carboxamido]benzoic acid (ITY1115), RAR agonists disclosed in J. Med. Chem., 48(19), pp. 5875-5883, 2005, RAR agonists disclosed in U.S. Patent Publication No. 0149737A1/2012, RAR agonists disclosed in WO 2009/22720, and RAR agonists disclosed in WO 2009/22721. According to the present invention, RAR agonist preferably has least RARα agonistic action. Among the aforementioned examples, Am80 is preferably used as the RAR agonist.

According to the present invention, the RXR agonist can be chosen from the group consisting of 4-[5H-2,3-(2,5dimethyl-2,5-hexano)-5-methyldibenzo[b,e]-diazepin-11-yl] benzoic acid (HX630) and structurally similar analogues thereof, 6-[1-(3,5,5,8,8-pentamethyl-6,7dihydronaphthalen-2-yl)cyclopropyl]pyridine-3-carboxylic acid (LG1069). RXR agonists disclosed in Biochimica et Biophysica Acta, 1821, pp. 21-56, 2012, RXR agonists disclosed in Biochimica et Biophysica Acta, 1821, pp. 57-69, 2012, and RXR agonists disclosed in WO 2009/22722. Among the aforementioned examples, HX630 can be preferably used as the RXR agonist.

The medicament of the present invention comprises, as an active ingredient, a combination of a combination of a retinoic acid receptor (RAR) agonist and a retinoid X receptor (RXR) agonist. The medicament of the present invention can be provided as a single dosage form that comprises the combination of a combination of a retinoic acid receptor (RAR) agonist and a retinoid X receptor (RXR) agonist. Alternatively, the medicament of the present invention can be provided as a combination of a single dosage form that comprises a retinoic acid receptor (RAR) agonist and a single dosage form that comprises a retinoid X receptor (RXR) agonist. In that case, the two kind of dosage forms can be administered to a mammal simultaneously, or separately with an appropriate interval time. Each effective dose of a retinoic acid receptor (RAR) agonist and a retinoid X receptor (RXR) agonist in the combination can be appropriately chosen by those skilled in the art in view of the examples in the specification, and generally determined in view of each effective dose as an agonist described in the references cited in the specification.

As the retinoic acid receptor (RAR) agonist or the retinoid X receptor (RXR) agonist, a pharmacologically acceptable salt, a hydrates, or a solvate can be used, as well as free form of the agonist. As the medicament of the present invention, the aforementioned combination of the retinoic acid receptor (RAR) agonist or the retinoid X receptor (RXR) agonist, per se, may be administered. However, a pharmaceutical composition for oral administration or parenteral administration comprises the combination or each of the agonists may preferably be administered which can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, suppositories, inhalants, eye drops, nasal drops, ointments, creams, patches and the like.

The aforementioned pharmaceutical compositions may be prepared by using pharmacologically and pharmaceutically acceptable additives. Examples of pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like.

The doses of the medicament of the present invention are not particularly limited, and they can suitably be selected depending on strength of the agonistic action and the like, and also can suitably be increased or decreased depending on various factors to be generally considered, for example, the body weight or age of a patient, the kind of symptoms of Alzheimer's disease, an administration route and the like. For example, for oral administrations, the medicament may be used in a dose of from 0.01 to 1,000 mg per day for an adult as a weight of each of RAR agonist and RXR agonist.

EXAMPLES

The present invention will be more specifically explained by referring to the following examples. However, the scope of the present invention will not be limited to the details of the examples.
Materials And Methods
Compounds Tamibarotene (also known as Am80) and HX630 were prepared as previously described [31, 32]. GW9662 was obtained from Cayman Chemical (Ann Arbor, Mich., USA). These compounds were dissolved in DMSO for in vitro study (stock solution: 10 mM).
Animals Hemizygous APP23 mice, which overexpress human-type AβPP carrying the double mutation K670N/M671L, were produced and bred as previously described [33]. Only male mice were analyzed. Wistar rats were obtained from Kyudo Co., Ltd. (Kumamoto, Japan). Animals were housed in standard mouse cages under standard laboratory conditions: food and water available ad libitum, constant room temperature and humidity, and a 12 h light/12 h dark cycle (light on from 08:00 to 20:00). These animal experiments were conducted according to the guidelines of the Ministry of Education, Culture, Sports, Science, and Technology of Japan, and were approved by the Institutional Animal Care and Use Committee of Kumamoto University (#B25-133).
Cell Culture Primary microglia (type 1) were harvested from primary mixed glial cell cultures prepared from neonatal Wistar rat pups, as previously reported [34]. Mouse microglial cell line MG5 and mouse glial cell line A1 were maintained as previously described [35]. Mouse neuroblastoma cell line N1E-115 and Neuro 2a (American Type Culture Collection, Manassas, Va., USA) were maintained in Dulbecco's modified Eagle's medium (DMEM) supplemented with 10% fetal bovine serum (FBS), 20 U/ml penicillin (Invitrogen, Gaithersburg, Md., USA), and 20 μg/ml streptomycin (Invitrogen). Primary rat microglia were treated with Am80 (5 μM) and/or HX630 (5 μM) in the presence and absence of GW9662 (10 μM) for 48 h in Eagle's MEM supplemented with 10% FBS and 0.2% glucose. MG5 cells and A1 cells were treated with Am80 (5 μM) and/or HX630 (5 μM) for 48 h in DMEM containing 10% FBS. N1E-115 cells were treated with Am80 (5 μM) and/or HX630 (5 μM) for 5 days in DMEM containing 2% FBS.

Since the effective concentration of Am80 in vivo has not been determined, we considered that a relatively high concentration of Am80 should be used in the in vitro study in order to ensure adequate stimulation. When we investigated RARE-luciferase activity in Neuro2a cells, Am80 in the concentration range of 0.2-5 μM hardly altered the RARE activity (Supplementary FIG. 1). Moreover, the combination of HX630 (5 μM) with Am80 in the range of 0.2-5 μM also had little effect. Therefore, the concentrations of Am80 and HX630 were both set at 5 μM for the in vitro study.
Cell Assays $^{125}$I-Labeled oligomeric $Aβ_{1-42}$ (o-$Aβ_{1-42}$) was prepared as described [34]. Cells were cultured in 24-well plates for 48 h in Eagle's MEM supplemented with 10% FBS in the presence or absence of Am80 (5 μM) and HX630 (5 μM). After the 48-h treatment, the cells were washed twice with labeling medium (DMEM containing 3% BSA) and then incubated with $^{125}$I-labeled o-$Aβ_{1-42}$ for 6 h at 37° C. Following the 6-h incubation, medium was removed from each well, and soluble radioactivity in TCA (degraded and extracellularly released peptide fragments) was determined as an index of Aβ degradation in the medium as described previously [34]. The Aβ degradation activity may thus include both receptor-mediated phagocytic activity and extracellular protease-mediated degradation. Cells were washed three times with PBS, then lysed with 0.4 ml of 0.1 M NaOH for 30 min at 37° C., and cell-associated (including cell-incorporated) radioactivity and cell proteins were determined with an autogamma counter and the BCA Protein Assay Reagent (Pierce), respectively. We could not determine the activity of IDE-dependent degradation in this medium, because the incubation medium was replaced with labeling medium prior to incubation with $^{251}$I-o-Aβ.

Drug Administration

APP23 mice begin forming amyloid deposits when they are 6 months old, but memory deficits in the MWM test appear quite early (before 3 months of age) [36]. Here, we used 8.5-month-old male APP23 mice and their WT littermates (C57BL/6J). We used stratified random sampling to divide mice (four to six per cage) into four groups to equalize the mean body weight of the study groups: mice given 0.5 mg/kg/d Am80, those given 5 mg/kg/d HX630, those given the mixture of 0.5 mg/kg/d Am80 and 5 mg/kg/d HX630, and those given the vehicle. Am80 and HX630 were suspended in 0.5% (w/v) carboxymethylcellulose solution and were orally administered to mice at 0.5 mg/kg (Am80) or 5 mg/kg (HX630) for 17 consecutive days (once daily at 18:00). Control animals received the same volume of 0.5% (w/v) carboxymethylcellulose solution orally, without the other compounds. We set the 0.5 mg/kg/d dose for Am80 on the basis that this had been found effective in other in vivo studies, such as those by Kawahara et al. [15] and Ishido and Shudo [37]. Higher doses of Am80 (3 mg/kg/d and 6 mg/kg/d) were also orally administered to mice for 17 consecutive days. Animals were weighed once a week. Mice were subjected to behavioral testing on days 15-18 of the first oral administration of the compounds (at 19:00-23:00). On days 15-17 (not day 18), animals received the compounds at 24:00, after behavioral testing. On the last day of behavioral testing (day 18), animals received no compounds and tissues were sampled.

The Morris Water Maze (MWM) Test

The MWM test was performed as described previously [15, 38]. For this test, administered during the 12 h dark period, a circular, 150-cm-diameter pool (40 cm high) was filled with water maintained at 23.0±1° C. A 12-cm-diameter round platform was placed in one quadrant and was kept 1 cm below the water surface. During acquisition training, mice completed three to five trials daily for 4 consecutive days: day 1:3 trials, day 2:3 trials, day 3:5 trials, and day 4:4 trials. The trials began at three different positions in semi-random order, and intertrial intervals were 20 min. A mouse that could not find the platform in 120 s was carefully guided to the platform and was allowed to stay there for 20 s. A probe trial followed the acquisition phase: the platform was removed from the maze, and mice were permitted to swim freely for 100 s. During both acquisition and probe trials, the routes of the mice were recorded by means of a computerized video tracking system (CompACT VAS; Muromachi Kikai Co. Ltd., Tokyo, Japan). Training trials measured the time it took for a mouse to find the escape platform. Probe trials determined the percent time spent in each quadrant of the maze. The number of times that a mouse crossed over the training annulus (diameter of 22 cm), which was 3.1 times the size of the target platform, was also used to analyze performance in the probe trial. In this study, the probe trial was administered at 2 h after the last training trial. Spatial memory retention of the platform position is considered to reflect short-term memory [39].

Animal Tissue Sampling

After the behavior analysis (at 2 h after the probe trial), mice were anesthetized with an injection of Somnopentil (50 mg/kg, given intraperitoneally; Kyoritsu Seiyaku, Tokyo, Japan), after which they were perfused transcardially with 30 ml of PBS. Brains were rapidly removed and divided into hemispheres. One hemisphere was snap-frozen in liquid nitrogen for protein analysis. The other hemisphere was snap-frozen in liquid nitrogen for total RNA assay. In some experiments, a hemisphere was divided under a stereomicroscope into four sections: cerebral cortex, hippocampus, cerebellum, and other regions, each of which was snap-frozen in liquid nitrogen and stored at −80° C. until use. The number (n) of mice used for experiments is shown in each figure.

Immunoblot Analysis

Rat primary microglia and mouse microglial MG5 cells ($5 \times 10^6$ cells per 100-mm dish) were homogenized in RIPA buffer [10 mM Hepes-NaOH (pH 7.4) containing 150 mM NaCl, 1 mM EDTA, 1% Triton X-100, 0.5% sodium deoxycholate, 0.1% SDS, 1 mM PMSF, 1 mg/ml leupeptin. 1 mg/ml pepstatin A, and 10 mg/ml soybean trypsin inhibitor]. After centrifugation of samples, supernatants were separated by SDS-PAGE and proteins were electrotransferred to nitrocellulose membranes. The cerebral hemispheres and hippocampus were homogenized in 3 volumes (w/v) and 10 volumes (w/v), respectively, of 50 mM Tris-HCl buffer (pH 7.6) containing 150 mM NaCl, 1 mM PMSF, 1 mg/ml leupeptin, 1 mg/ml pepstatin A, and 10 mg/ml soybean trypsin inhibitor. Triton X-100-solubilized membrane fractions of the cerebral hemispheres were prepared as described previously [40]. Aliquots of homogenates and membrane fractions were saved for determination of protein, and, after addition of 25 mM DTT, samples were incubated at 60° C. for 10 min. The samples (40 μg homogenate or 5.0 μg membrane fraction) were then subjected to SDS-PAGE, and proteins were electrotransferred to nitrocellulose membranes. These membranes were incubated with Tris-buffered saline (TBS) (pH 7.4) containing 2% dehydrated skimmed milk to block nonspecific protein binding. Membranes were then incubated with antibodies to CD36 (BAF2519, 1:500 dilution; R&D Systems), NEP (H-321, 1:100 dilution; Santa Cruz Biotechnology, Santa Cruz, Calif., USA), IDE (PC730, 1:1000 dilution; Calbiochem, Darmstadt, Germany; 9B12, 1:1000 dilution; Abcam, Cambridge, UK), IL-4 receptor α chain (IL-4Rα) (S-20, 1:200 dilution; Santa Cruz Biotechnology), Aβ$_{1-17}$ (6E10, 1:500 dilution; Chemicon International, Temecula, Calif., USA), scavenger receptor class AI/AII (SRA) (SRA-E5, 1:1000 dilution; a gift from Prof. M. Takeya at Kumamoto University, Kumamoto, Japan), or β-actin (AC15, 1:5000 dilution; Sigma), followed by secondary antibodies: horseradish peroxidase-linked antibodies against rabbit, goat, or mouse Ig (each diluted 1:1000). Bound horseradish peroxidase-labeled antibodies were then detected via chemiluminescence (an ECL kit; Pierce, Rockford, Ill., USA). Protein concentrations were determined with the BCA Protein Assay Reagent (Pierce) and Bradford Protein Assay Reagent (Pierce).

Immunohistochemistry

Mice were anesthetized with pentobarbital, and 4% PFA in PBS was perfused through the left cardiac ventricle. Brains were removed and embedded in paraffin, before being cut into 4 μm thick sections, which were then deparaffinized and incubated with 0.01% (w/v) 1-fluoro-2,5-bis (3-carboxy-4-hydroxystyryl)benzene (FSB, a reagent for amyloid staining; Dojindo, Kumamoto, Japan) for 30 min. After washing with 50% ethanol, the sections were autoclaved (at 120° C.) in 10 mM citrate buffer (pH =6.0) for 5 min, and washed in PBS. For Aβstaining (6E10), sections were immersed in 70% formic acid for 10 min. The sections were then incubated with primary antibodies to RARα (rabbit IgG, C-20, 1:100 dilution; Santa Cruz Biotechnology), RARβ (rabbit IgG, C-19, 1:100 dilution; Santa Cruz Biotechnology), Aβ$_{1-17}$ (mouse IgG, 6E10, 1:500 dilution; Chemicon International, Temecula, CA, USA), Iba1 (rat serum, 1:500 dilution; generated against a synthetic peptide corresponding to a specific sequence of mouse Iba1: CNKEHKRPTGPPAKKAISELP (SEQ ID NO: 25) (near the C-terminus)), or GFAP (chicken IgY, GTX85454, 1:200 dilution; GeneTex), followed by the corresponding Alexa Fluor 488- or 594-labeled secondary antibodies (1:300 dilution; Molecular Probes and Abcam). For immunohistochemistry with anti-Iba1 antibody, we used a tyramide signal amplification system (Molecular Probes) according to the manufacturer's recommendations. Specimens were mounted with VECTASHIELD mounting medium (Vector) and were examined with a confocal laser-scanning microscope (FluoView; Olympus).

For immunohistochemical staining with IL-4Rα, the avidin-biotin peroxidase technique was used. Mice were anesthetized with pentobarbital, and 4% PFA in PBS was perfused through the left cardiac ventricle. Brains were removed and cryoprotected in sucrose. Frozen sections (10-μm thick) were cut with a cryostat and thaw-mounted on gelatin-coated slides. The coronal sections were immersed in 10 mM citrate buffer (pH=6.0) and were autoclaved (at 80° C.) for 5 min. Endogenous peroxidase was blocked by treatment with 1% $H_2O_2$ in methanol for 15 min, followed by overnight incubation at 4° C. with rabbit anti-IL-4Rα antibody (S-20, 1:100 dilution; Santa Cruz Biotechnology). Rabbit IgG from non-immune serum was used as a negative control. Excess antibody was washed out with PBS, and the sections were incubated for 1 h with the corresponding biotinylated secondary antibody (1:200 dilution, Chemicon International). The sections were then incubated for 30 min at room temperature with avidin-peroxidase complex (Vector). Peroxidase was visualized by incubation with diaminobenzidine solution with nickel enhancement.

Elisa

The TBS-soluble (TBS-extractable) fraction and the TBS-insoluble (but guanidine HC1-extractable) fraction from the cerebral hemispheres or hippocampus were prepared as described previously [15, 41]. The amounts of $Aβ_{40}$ and $Aβ_{42}$ in each fraction were determined by using sandwich ELISAs (294-64701 and 290-62601 (Wako), respectively), according to the manufacturer's instructions. The amounts of tumor necrosis factor-α (TNF-α) and IL-4 in the TBS-soluble fractions of cerebral cortex and hippocampus were analyzed by means of sandwich ELISAs KMC3012 (Invitrogen) and ELM-IL-4-001 (RayBiotech, Inc., Norcros, Ga., USA), respectively, according to the manufacturer's instructions. Protein concentrations were determined with the Bradford Protein Assay Reagent (Thermo Fisher Scientific Inc., Rockford, Ill., USA), with BSA as the standard.

RT-PCR Analysis

Total RNA from the cerebral hemispheres, hippocampus, or MG5 cells was prepared by guanidinium thiocyanate-phenol-chloroform extraction [42]. Then, 1.0 μs of total RNA was converted to cDNA with SuperScript III Reverse Transcriptase (Invitrogen) and nucleotide random primer (Invitrogen). Quantitative real-time PCRs were carried out by using the LightCycler 1.5 system (Roche, Mannheim, Germany) with the FastStart DNA Master SYBR Green I LightCycler kit (Roche). The primers used were as follows: for Ide: sense primer, 5'-CGGCCATCCAGAGAATAGAA-3' (SEQ ID NO: 1) and antisense primer, 5'-TTTGGAGGGTCTGACAGTGA-3' (SEQ ID NO: 2); for Il4rα: sense primer, 5'-CCTCACACTCCACACCAATG-3' (SEQ ID NO: 3) and antisense primer, 5'-CCTGGGTTCCTTGTAGGTCA-3' (SEQ ID NO: 4); for Tnf receptor (Tnfr)1: sense primer, 5'-ACGGCTTCCCAGAATTACCT-3' (SEQ ID NO: 5) and antisense primer, 5'-TCAGCTTGGCAAGGAGAGAT-3' (SEQ ID NO: 6); for Tnfr2: sense primer, 5'-TACCAAGGGTGGCATCTCTC-3' (SEQ ID NO: 7) and antisense primer, 5'-AGGGCTTCTTTTTCCTCTGC-3' (SEQ ID NO: 8); for RARα (ramα): sense primer, 5'-TTCTTTCCCCCTATGCTGGGT-3' (SEQ ID NO: 9) and antisense primer, 5'-GGGAGGGCTGGGTACTATCTC-3' (SEQ ID NO: 10); for RARβ (rarβ): sense primer, 5'-CTGCTCAATCCATCGAGACAC-3' (SEQ ID NO: 11) and antisense primer, 5'-CTTGTCCTGGCAAACGAAGC-3' (SEQ ID NO: 12); for tissue-plasminogen activator (tPA): sense primer, 5'-ATGAGGCATCGTCTCCATTC-3' (SEQ ID NO: 13) and antisense primer, 5'-ACAGATGCTGTGAGGTGCAG-3' (SEQ ID NO: 14); and for β-actin: sense primer, 5'-CTAAGGCCAACCGTGAAAAG-3' (SEQ ID NO: 15) and antisense primer, 5'-ACCAGAGGCATACAGGGACA-3' (SEQ ID NO: 16). A standard curve for each gene was generated with serial dilutions of the respective PCR product. Expression was normalized against the expression of β-actin. PCR specificity was confirmed by means of sequencing, gel electrophoresis, and melting curve analysis.

For semi-quantitative RT-PCR analysis, PCRs were carried out with Quick Taq HS DyeMix (DTM-101; Toyobo Co. Ltd., Osaka, Japan). The primers used were as follows: for Cd36: sense primer, 5'-AGGTCCTTACACATACAGAGTTCG-3' (SEQ ID NO: 17) and antisense primer, 5'-GGACTTGCATGTAGGAAATGTGGA' (SEQ ID NO: 18); for membrane metallo-endopeptidase (Mme)/Nep: sense primer, 5'-CAGCCTCAGCCGAAACTACA-3' (SEQ ID NO: 19) and antisense primer, 5'-TTTGTCTCAGCATCCATCCAA-3' (SEQ ID NO: 20); for Ide: sense primer, 5'-CGGCCATCCAGAGAATAGAA-3' (SEQ ID NO: 21) and antisense primer, 5'-TTTGGAGGGTCTGACAGTGA-3' (SEQ ID NO: 22); for β-actin: sense primer, 5'-CTAAGGCCAACCGTGAAAAG-3' (SEQ ID NO: 23) and antisense primer, 5'-ACCAGAGGCATACAGGGACA-3' (SEQ ID NO: 24). The primer sets for Cd36, Mme, Ide, and β-actin were expected to give PCR products with sizes of 789, 255, 172, and 104 bp, respectively. Semi-quantitative PCR consisted of an initial denaturation cycle at 94° C. for 2 min, followed by 40 cycles for Cd36, 35 cycles for Mme, 30 cycles for Ide, and 26 cycles for β-actin. An additional cycle at 72° C. for 7 min completed the amplification. Amplified PCR products were separated by 2% (except for Cd36, 1.5%) agarose gel electrophoresis and visualized by staining with ethidium bromide. Densitometric quantification was done with the Image Gauge software program (Fuji Photo Film Co., Tokyo, Japan). Expression was normalized against the expression of β-actin. PCR specificity was confirmed by means of sequencing and gel electrophoresis.

Transient Transfection and Reporter Gene Assay

MG5 cells ($2×10^6$ cells in 100 μl) were transfected by electroporation with 1.0 μg of pGL3-RARE-Luc (#13458; Addgene) or pGL3-Luc vector (Promega) and 0.25 μg of Renilla luciferase vector (phRL-TK) (Promega), using the Nucleofector transfection system (program #D-032; Amaxa) according to the manufacturer's protocol, taken up in the medium, and seeded in 48-well plates ($1.25×10^5$ cells/well). For some experiments, cells were transfected with 1.0 μg of pGL3-RARE-Luc or pGL3-Luc vector and 0.25 μg of phRL-TK in the presence of 0.25 μg each of pcDNA3.1-RAR (#16287; Addgene) and pcDNA3.1-RXR (#8882; Addgene). An empty pcDNA3.1 expression vector was used to maintain equal amounts of DNA for each transfection. Five hours after transfection, the cells were exposed to Am80 (5 μM) and/or HX630 (5 μM) in the medium for 24 h. Luciferase activities were determined in cell lysates. Firefly luciferase activity was normalized to that of Renilla luciferase for each well.

Neuro2a cells were seeded in 24-well plates ($2\times10^5$ cells/well) and transfected with 0.2 μg of pGL3-RARE-Luc (#13468; Addgene) or pGL3-Luc vector (Promega) and 0.05 μg of Renilla luciferase vector (phRL-TK) (Promega), using Effectene reagent (Qiagen) according to the manufacturer's protocol. Five hours after transfection, cells were exposed to Am80 (5 μM) and/or HX630 (5 μM) in the medium for 24 h. Luciferase activities were determined in cell lysates. Firefly luciferase activity was normalized to that of Renilla luciferase for each well.

Statistical Analysis

All data were expressed as means±SEM. For statistical comparisons of the means between two groups, Student's t-test was applied after confirming the equality of group variances. In factorial ANOVA, drug treatment (vehicle, Am80, HX630, or Am80/HX630) was used as a between-subject factor and the training regimen (days or trials) was used as a within-subject (repeated measures) factor. The Bonferroni multiple comparison test was used after two-way ANOVA. For comparisons of three or more groups, Dunnett's multiple comparison test was applied after one-way ANOVA. To determine whether a correlation between variables existed, a scatterplot and Pearson correlation analyses were employed. All statistical analyses were performed with GraphPad Prism (GraphPad Software). Significance was defined as P value <0.05.

Results

Co-Administration of Am80 with HX630 Reversed Deficits in Spatial Learning and Memory in 8.5-Month-Old APP23 Mice We orally administered tamibarotene/Am80 (a selective RARα,β agonist with little or no binding affinity for RARγ and RXRs, 0.5 mg/kg), HX630 (a pan RXRs agonist, 5 mg/kg), or their combination to 8.5-month-old APP23 mice (an AD model) and their WT littermates for 17 days (FIG. 1A). During the experimental period, body weights of the mice in the different groups showed no significant difference (data not shown). Vehicle-treated APP23 mice showed considerably impaired acquisition of spatial learning (i.e., a longer escape latency) in the MWM test, compared with WT littermates (FIG. 1B; P<0.001 by two-way ANOVA). However, co-administration of Am80 with HX630 to APP23 mice led to a significant improvement in this measure compared with vehicle-injected control APP23 mice (FIG. 1B; P<0.001 by two-way ANOVA). In addition, a post hoc comparison indicated that significant improvement was detected only in the co-administration group, not in groups treated with either agonist alone (FIG. 1B; P<0.01). In the post hoc comparison among groups, Am80/HX630 co-treatment showed a significant improvement compared with either HX630 treatment (at days 2-4) or Am80 treatment (at days 2 and 3, but not at day 4).

After the acquisition trials, mice underwent probe trials to evaluate retention of memory of the platform location (FIG. 1C). Vehicle-treated APP23 mice spent a significantly shorter time in the target quadrant (17.1±3.6%) compared with vehicle-treated WT mice (33.0±3.2%) (FIG. 1C; P<0.01). However, Am80/HX630-treated APP23 mice spent a significantly longer time in the target quadrant (30.5±6.1%) than did vehicle-treated APP23 mice (FIG. 1C; P<0.05). In addition, Am80/HX630-treated APP23 mice spent a significantly longer time in the target quadrant than did HX630-treated mice (FIG. 1C; P<0.05). As expected, vehicle-treated APP23 mice had significantly fewer crossings over the training annulus (1.42±0.41) compared with vehicle-treated WT mice (3.90±0.65) (FIG. 1D; P<0.01). After co-administration of Am80 with HX630, however, APP23 mice had a significantly higher score (3.22±0.65) than did vehicle-treated APP23 mice (FIG. 1D; P<0.05). Thus, co-administration of Am80/HX630 rapidly improved memory deficits in middle-aged APP23 mice.

Co-Administration of am80 with HX630 Reduced TBS-Insoluble $A\beta_{40}$ and $A\beta_{42}$ Levels in APP23 Mouse Brains We used sandwich ELISA to determine and compare the amounts of $A\beta_{40}$ and $A\beta_{42}$ in Tris-buffered saline (TBS)-soluble and -insoluble brain fractions (FIG. 2). Administration of Am80 (0.5 mg/kg/d) or HX630 (5 mg/kg/d) or their combination for 17 days had no effect on levels of $A\beta_{40}$ and $A\beta_{42}$ in the TBS-soluble brain fraction of 8.5-month-old APP23 mice (FIG. 2A, C). In contrast, levels of $A\beta_{40}$ and $A\beta_{42}$ in TBS-insoluble brain fractions were significantly lower in the Am80/HX630-treated group than in the other three groups (FIG. 2B, D). These results indicate that reduction of insoluble Aβ in brain of Am80/HX630-treated mice was correlated with memory improvement. The Aβ levels in 8.5-month-old WT mice were not determined, because preliminary tests showed they were below the detection limit of the ELISA system (data not shown).

Am80/HX630 Increased Levels Of NEP And IDE Proteins In Vivo

Enzymatic degradation of Aβ peptides and microglia-mediated phagocytosis are involved in Aβ clearance, especially from insoluble fractions [43]. Activated microglia accumulated around amyloid plaques (Supplementary FIG. 2A-E) [43] and expressed RARα in vehicle-treated 8.5-month-old male APP23 mice (Supplementary FIG. 2A-E). Astrocytes also expressed RARα in the vicinity of amyloid plaque (Supplementary FIG. 2F-J). It is noteworthy that RARα staining in microglia was almost entirely localized in nuclei, in contrast to the uniformly stained astrocytes, suggesting that RARα was already activated in microglia. Immunoblot analysis of brain samples revealed that the level of scavenger receptor CD36 protein was increased in HX630-treated mice, but CD36 was not increased after co-administration of HX630 with Am80 (FIG. 3A). Higher levels of NEP protein were found in Am80-, HX630-, and Am80/HX630-treated APP23 mice than in vehicle-treated mice (FIG. 3A). The IDE protein level was indistinguishable among the four groups (FIG. 3A). However, the IDE protein level in the membrane-bound fraction was increased significantly in HX630- and Am80/HX630-treated APP23 mice compared with vehicle-treated APP23 mice (FIG. 3B; P<0.05). The Ide mRNA level was also increased significantly in Am80/HX630-treated APP23 mice compared with the vehicle-treated group (FIG. 3C; P<0.05). The Ide mRNA level also showed a slight increase in HX630-treated APP23 mice, but this was not statistically significant (FIG. 3C; P=0.062). These results suggest that IDE and NEP may be involved in the increased Aβ clearance in APP23 mice treated with Am80/HX630.

Am80/HX630 and HX630 Increased Clearance Activity of Oligomeric Aβ Peptide in Rat Primary Microglia We next investigated whether or not Am80 and HX630 increase phagocytotic activity of oligomeric Aβ peptide in microglia in vitro (FIG. 4). Recently, Yamanaka et al. [44] reported that a peroxisome proliferator-activated receptor (PPAR)γ agonist plus an RXR agonist additively up-regulated CD36 expression and enhanced microglial uptake of Aβ peptide. CD36 expression was increased 1.3-fold by HX630 treatment, but was not increased in Am80/HX630-treated cells (FIG. 4A). Similar results were also observed in vive (as shown in FIG. 3A). Cd36 is a target gene of PPARγ/RXR [45]. The increase in CD36 expression by HX630 in microglia was inhibited by co-incubation with the PPARγ antagonist GW9662 (FIG. 4A), indicating that HX630-induced CD36 expression is PPARγ/RXR-dependent. IDE was increased significantly only after co-treatment with Am80/HX630 (FIG. 4A). HX630 and Am80/HX630 increased degradation activity towards $^{125}$I-labeled oligomeric A$\beta_{1-42}$ (o-A$\beta_{1-42}$) in rat primary microglia, compared with vehicle-treated cells, and the increase was inhibited by fucoidan, a scavenger receptor inhibitor, in each case (FIG. 4B). The cell-association and degradation activities in Am80/HX630-treated cells were also inhibited by insulin, an IDE inhibitor (FIG. 4C, 4D). The NEP inhibitor thiorphan did not affect the degradation activity in Am80/HX630-treated cells (FIG. 4D). Thus, scavenger receptor-mediated uptake, intracellular degradation and Aβ catabolism by IDE (in cytosol and/or on plasma membrane) are important for Am80/HX630-induced clearance of o-A$\beta_{1-42}$.

Improvement in Memory of Am80/HX630-Treated APP23 Mice is Correlated with IL-4 Levels in the Hippocampus We next investigated whether Am80/HX630-induced memory improvement is related to reduced neuroinflammation, especially changes in levels of anti-inflammatory cytokine IL-4, in the cerebral cortex and hippocampus (FIG. 5). Although the IL-4 level in the cortex was indistinguishable in vehicle-treated WT and APP23 mice, the hippocampal IL-4 level was significantly higher in APP23 mice than in WT mice (FIG. 5A; P<0.05). HX630 and Am80/HX630 treatments increased the hippocampal IL-4 levels of APP23 mice, but the increase was statistically insignificant (FIG. 5A; P=0.096 and P=0.087, respectively). However, the hippocampal IL-4 level in Am80/HX630-treated APP23 mice showed a significant positive relationship with memory in the MWM test (FIG. 5Bb; P=0.007, r=0.625). No such correlation was observed for groups treated with vehicle or a single retinoid (FIG. 5Ba, Supplementary FIG. 3). The vehicle-treated WT mice also showed a positive correlation between the hippocampal IL-4 level and the MWM memory test performance (P=0.072, r=0.772 for target occupancy, P=0.033, r=0.849 for crossings over the target annulus) (Supplementary FIG. 4A,B).

Hippocampal levels of insoluble A$\beta_{42}$a were decreased in Am80/HX630-treated APP23 mice (FIG. 5C). These results suggest that memory performance may depend upon the efficiency of IL-4 signaling, not the cytokine levels (FIG. 5A), and that Am80/HX630-induced co-activation of RARα,β/RXRs improves IL-4 signaling.

Am80 and HX630 Synergistically Increased IL-4Rα Expression in Mouse Microglial MG5 Cells To investigate whether the combination of Am80 and HX630 increases the expression of IL-4 receptor α chain (IL-4Rα) in microglial cells, we examined their effects in vitro on mouse microglial MG5 cells (FIG. 6). Am80 and HX630 alone did not increase IL-4Rα levels, but their combination did result in an increase of IL-4Rα (FIG. 6A). IL-4RαmRNA in MG5 cells was also increased 24-48 hours after Am80/HX630 co-treatment (FIG. 6B). RA response element (RARE) reporter activity in MG5 cells was increased 4.3-fold after Am80 treatment (FIG. 6C), but no increase was seen after HX630 treatment. However, this activity showed a marked increase (15.9-fold) after co-treatment with HX630 and Am80 (FIG. 6C). In contrast, Am80/HX630 had no effect on the luciferase activity of the control pGL3-luc vector, as expected (FIG. 6C). These results indicate that HX630 has an RAR-synergistic effect in MG5 cells and that marked RAR activity induced by Am80/HX630 may be involved in IL-4Rα up-regulation in MG5 cells.

The above results demonstrate that oral co-administration of HX630 (5 mg/kg) and Am80 (0.5 mg/kg) for 17 days ameliorated learning deficits in 8.5-month-old APP23 mice (FIG. 1) and significantly reduced brain levels of insoluble A$\beta_{42}$ and A$\beta_{40}$ (FIG. 2). Administration of Am80 alone at higher dose (3 mg/kg/d or 6 mg/kg/d for 17 days) neither reduced Aβ levels nor improved cognitive deficits in APP23 mice (Supplementary FIG. 5, data not shown).

In contrast, Ding et al. [14] demonstrated that administration of RARs agonist ATRA alone improved memory function in APP/PS1 mice. However, ATRA is shown to isomerize to the 9-cis isomer in vitro [46], which is a potent RARs/RXRs dual agonist, whereas synthetic retinoid Am80 is not converted to derivatives with RXR affinity [47]. Solomin et al. [48], using an RXR-specific reporter transgene, have provided evidence that ATRA (20 mg/kg) activates RXR in vivo. An RXR-selective agonist, bexarotene (100 mg/kg, p.o.), improved behavioral defects in APP/PS1 mice [16], but it displays cross-reactivity with RARs at higher concentrations [49]. Shudo et al. [13] previously reported that co-administration of Am80/HX630 efficiently ameliorates memory deficits in scopolamine-treated rats, a model of the main clinical symptom of AD. Therefore, it is reasonable to consider that effective memory improvement by retinoids may require RARs/RXRs co-activation. Participation of RARγ is not required for this retinoid-induced improvement in memory deficits, because Am80 is specific for RARα and RARβ and hardly binds to RARγ [50]. Consideration of retinoid receptor selectivity is therefore important for the therapeutic use of retinoids.

Co-administration of Am80 with HX630 reduced the brain level of insoluble, but not soluble, Aβ in APP23 mice (FIG. 2). Soluble (TBS-extractable) Aβ is localized mainly in neurons, whereas insoluble Aβ accumulates in extracellular plaques that are formed via oligomers or protofibrils [41, 51]. It is thought that both intracellular and extracellular Aβ oligomers contribute to the pathology of AD [52]. Tomiyama et al. [52] showed that intraneuronal Aβ oligomers are fractionated predominantly into TBS-insoluble fractions, particularly the formic acid-extracted fraction, in AβPP transgenic mice expressing the E693Δ mutation, and contribute to AD via enhanced Aβ oligomerization without fibrillization. Our results here indicate that the apparent reduction of insoluble Aβ correlates well with memory improvement in APP23 mice. Mechanisms that may lead to reduced insoluble Aβs consisting intracellular/extracellular Aβ oligomers and extracellular Aβ plaques include the following: (1) increased expression of Aβ-degrading enzymes such as NEP and IDE in neurons and glial cells, and (2) increased internalization or clearance of oligomeric Aβs mainly in microglia. We demonstrated here that these two mechanisms are both functional in retinoid ligand-treated APP23 mice.

With regard to the first mechanism, we found that Am80/HX630 treatment increased the expression of the Aβ-degrading enzymes IDE and NEP in vivo (FIG. 3). We also observed that Am80/RX630 treatment increased both NEP and IDE in murine N1E115 neuronal cells, and increased NEP in murine A1 glial cells (Supplementary FIG. 6). IDE transcription is regulated by RA; the Ide gene contains a RARE in its promoter region [53]. We found that Am80/HX630 significantly increased Ide mRNA in APP23 mice (FIG. 3C). In addition, HX630 tended to increase Ide mRNA in APP23 mice (FIG. 3C; P=0.062). It is of note that membrane-associated IDE was increased in Am80/HX630- and HX630-treated APP23 mice, in parallel with the increase of Ide mRNA (FIG. 3B,C), although the IDE level in whole brain lysates was unchanged (FIG. 3A). It has been reported that there are two pools of IDE: a cytosolic pool with a longer half-life and a plasma membrane pool that shows faster turn-over [54]. The membrane-bound IDE protein level is important because its level is related to the clearance of Aβ plaques in APP tranagenic mice [55] and its decrease in the brain of individuals is associated with6 a high risk of developing AD [56]. Therefore, the increase in membrane-associated IDE that we observed is considered to contribute to Aβ clearance in Am80/HX630-treated APP23 mice. Qui et al. [57] showed that BV2 microglial cells secrete IDE, which mediates the degradation of Aβ peptides in the extracellular milieu. In addition, Goncalves et al. [17] showed that IDE activity in the medium was increased in murine microglial cells treated with Am580, an isomer of Am80. Therefore, there is a possibility that IDE is released extracellularly after Am80/HX630 treatment, although the activity in the medium could not be determined in our cell assay system.

NEP, another Aβ-degrading enzyme, was also increased after treatment with Am80, HX630, and their combination in APP23 mice (FIG. 3A). The Mme/Nep mRNA level, however, was unaffected by these retinoids in vivo and in vitro (Supplementary FIG. 7, data not shown), which suggests that retinoids increase either the translation of Mme/Nep mRNA or the stability of the NEP protein. RA reportedly increased RARα-mediated translation of glutamate receptor 1 mRNA in hippocampal neurons [58, 59], and RARα was present in nuclei and dendrites of hippocampal CA1 pyramidal neurons [59], where NEP immunoreactivity was detected in APP23 mice [60]. Our results suggest that increased expression of NEP may also contribute to reduction of insoluble Aβ in brain, although NEP expression is not specifically increased by co-administration of Am80/HX630.

It remains unknown whether neprilysin is a target gene of RAR or RXR. It has been reported that neprilysin is a target gene of PPARδ/RXR [61]. It is possible that up-regulation of neprilysin by HX630 treatment may depend on PPARδ/RXR activation. In this study, we showed that Am80 as well as Am80/HX630 increased the expression of neprilysin in APP23 mice. Further studies are required to elucidate whether neprilysin is a direct target gene of RAR/RXR.

Apropos the second mechanism, we found that HX630 and Am80/HX630 increased phagocytotic activity for oligomeric Aβ peptide in microglia in vitro (FIG. 4B). Therefore, increased microglial degradation and clearance of Aβs contribute to the reduction of insoluble Aβ in APP23 mice after HX630 and Am80/HX630 treatments. Recently, Yamanaka et al. [44] reported that a PPARγ agonist plus an RXR agonist additively up-regulated CD36 expression and enhanced microglial uptake of Aβ peptides. HX630 treatment increased CD36 protein level in microglia (FIG. 4A), suggesting that CD36 may be involved in Aβ clearance in HX630-treated microglia. However, the HX630-induced increase of CD36 expression was abolished by co-treatment with Am80 in vitro (FIG. 4A) and in vivo (FIG. 3A). In addition, the Cd36 mRNA level was decreased in Am80/HX630-treated APP23 mice (Supplementary FIG. 7). We also observed that co-addition of GW9662, a PPARγ antagonist, with HX630 disturbed the HX630-induced CD36 up-regulation in microglia (FIG. 4A). Based on these results, we initially speculated that Am80 might block RXR/PPARγ activation by HX630. However, Am80 has been suggested (62) to inhibit Cd36 transcription in macrophages via mechanisms that are independent of PPARγ, because Am80 does not affect the reporter activity of PPARγ response element. The possibility remains that the Am80-RARα/β complex may outcompete PPARγ for RXR. Thus, the precise mechanism(s) of Am80 inhibition of HX630-induced CD36 expression remains to be solved. We also demonstrated that IDE expression was increased in Am80/HX630-treated microglia, where CD36 expression was decreased (FIG. 4A). The increase of Aβ clearance activity was inhibited by insulin and fucoidan (FIG. 4C). These results indicate that IDE contributes to the Am80/HX630-induced increase of Aβ clearance by enhancing Aβ degradation in microglia.

Thus, we have shown that several factors—Aβ degradation or Aβ clearance systems involving IDE and NEP—are implicated in the reduction of insoluble Aβ and the improvement in memory that we observed in Am80/HX630-treated APP23 mice. All these factors together may be responsible for these effects, though we cannot yet assign a priority order for their contributions.

Regarding the participation of inflammation-related cytokines, the hippocampal IL-4 levels and MWM memory test performance showed a significant positive correlation in Am80/HX630-treated APP23 mice (FIG. 5Bb), whereas no such correlation was found in the vehicle-treated APP23 mice group. The vehicle-treated APP23 mice also had higher levels of hippocampal IL-4 than did vehicle-treated WT mice with normal memory function (FIG. 5A), suggesting that functional IL-4 signaling may be impaired in hippocampus of 8.5-month-old APP23 mice, and that the APP23 mice produce more IL-4 to compensate for the functional defect. We previously showed that intracerebral microinjection of IL-4/IL-13 reduced Aβ levels and improved cognitive deficits in APP23 mice, possibly by activating IL-4Rα-positive M2-like microglia [63]. Th2-biased immune responses induced by retinoids may serve to restore IL-4 signaling [23]. A candidate target gene that is impaired in APP23 mice is IL-4Rα, as has been reported for aged mice [64]. Immunohistochemical staining showed that IL-4Rα was expressed in the hippocampus (Supplementary FIG. 8A), as previously reported [65]. Moreover, the IL-4Rα protein level in the membrane fraction of whole brain, including hippocampus, was increased in Am80/HX630-treated APP23 mice compared to the vehicle-treated group (Supplementary FIG. 8B). We found here that Am80/HX630 increased IL-4Rα expression in microglial MG5 cells (FIG. 6A,B). Also, HX630 synergistically potentiated Am80-induced RAR activation in MG5 cells (FIG. 6C). Therefore, Am80/HX630 may promote differentiation of L-4-responsive M2-like microglia and increase their clearance activity for oligomeric Aβ peptides by restoring impaired IL-4 signaling in APP23 mice. The present results are consistent with reports that alternative microglial activation via IL-4 signaling is impaired in AD [3].

We have not determined whether IL-4Rα is a target gene of either RAR or RXR. However, Zhu et al. [66] showed that ATRA markedly increased mRNAs encoding RARβ and IL-4Rα in murine dendritic cells, and RARβ bound directly with the promoter region of IL-4Rα following ATRA treatment [66]. As shown in FIG. 6B, Rarβ mRNA was increased 6 h after Am80/HX630 treatment and reached a maximum at 24 h in murine MG5 microglial cells. On the other hand, IL-4Rα mRNA was expressed before treatment, then began to increase at 24 h after treatment, and remained little changed up to 48 h. These results suggest that the IL-4Rα induction is mediated by RARβ in Am80/HX630-treated cells. The Rarα gene contains RARE motifs in its promoter region [67, 68], and Rarα mRNA was also increased at 24-48 h after Am80/HX630 treatment (FIG. 6B). In Am80-treated MG5 cells, RARE-reporter activity was increased, but IL-4Rα protein expression remained unchanged (FIG. 6A, 6C). IDE protein, another target gene of RAR/RXR was increased by Am80/HX630, but not by Am80 in MG5 cells and rat microglia (FIG. 4A, Supplementary FIG. 9). These results suggest that co-activation of RAR/RXR might be required for efficient protein expression of RAR/RXR target genes in microglia.

Proinflammatory cytokines have been implicated in sickness-associated behaviors, aging, and autoimmunity [25], whereas cytokines associated with classical inflammation are required for many aspects of CNS function, such as synaptic scaling through glial TNF-α [69]. We observed that hippocampal TNF-α levels also showed a positive correlation with memory test performance in Am80/HX630-treated APP23 mice (Supplementary FIGS. 10Bd, 11Cd), but not in the vehicle-treated group (Supplementary FIGS. 10Ba, 11Ca). Levels of hippocampal mRNAs for Tnfr1 and 2 in APP23 mice were higher than those in WT mice (Supplementary FIG. 12A,B). Therefore, we believe that TNF-α signaling, not TNF-α amount (Supplementary FIG. 10A), may be impaired in APP23 mice. The present result is also consistent with reports that homeostatic synaptic scaling via TNF-α signaling is impaired in AD [70, 71].

In the present study, the hippocampal TNF-α level in Am80-treated APP23 mice showed a positive relationship with memory in the MWM test (P=0.084, r=0.827 for target occupancy, P=0.055, r=0.870 for crossings over the target annulus) (Supplementary FIGS. 10Bb, 11Cb). However, Am80 treatment did not ameliorate memory deficits in APP23 mice (FIG. 1), which suggests that improved hippocampal TNF-α signaling is important but not sufficient for memory improvement in 8.5-month-old APP23 mice. Consequently, co-activation of RAR and RXR by co-administration of Am80 with HX630 may ameliorate memory deficits in APP23 mice by improving both TNF-α and IL-4 signaling. However, further study is needed to confirm this idea.

The present in vivo data are not consistent with the in vitro study of Dheen et al. [72], who reported that Aβ peptide activates TNF-α expression, and also that this activation is reduced by ATRA treatment. However, the inhibitory effect of ATRA on TNF-α production was only moderate (about 40-50%), in contrast to its complete inhibition of nitric oxide production [72, 73]. In an AD model mouse, loss of both TNFR1 and TNFR2 exacerbates the pathogenesis and reduces Aβ phagocytic activity in microglia, indicating that intact TNF-α receptor signaling is critical for microglial-mediated uptake of the extracellular Aβ peptide pool [71]. Overall, these reports suggest that TNF-α produced by activated microglial cells is pleiotropic and may be either neuroprotective or neurotoxic depending on several factors, for example, which type of TNF receptor is activated [71, 74].

In this study, we observed that RARα is located in nuclei of microglia, but is dispersed throughout astrocytes in APP23 mice (Supplementary FIG. 2). Thus, when microglia accumulate around Aβ plaques in APP23 mice, their RARα appears to be activated, and Aβ clearance is increased. However, the ability of microglia to clear Aβ is considered to decrease with age and progression of AD pathology [75]. Goncalves et al. [17] recently showed that RARα signalling is down-regulated by Aβ, which inhibits the synthesis of the endogenous ligand, RA, in AβPP mice (Tg2576). Although we observed nuclear translocation of RARα in microglia of APP23 mice, this may be insufficient to enable transcriptional activation by endogenous RA in the mice, and exogenous Am80 may be required to achieve activation. We did not examine whether transcriptional activation of RARα is decreased in APP23 mice compared to their WT littermates. However, we observed that the expression level of mRNA for tissue-plasminogen activator (tPA), one of the genes controlled by RAR/RXR, tended to be lower than that in WT littermates (P=0.080, Supplementary FIG. 13B), whereas it was significantly increased in Am80/HX630-treated APP23 mice compared to vehicle-treated APP23 mice (Supplementary FIG. 13B). Moreover, Ide is a target gene of RAR/RXR, and Ide mRNA was decreased in microglia of APP/PS1 mice at the age of 8 months, compared to that in microglia of their WT littermates [75]. Further study is needed to investigate whether the expression levels of RARα-target genes in microglia are decreased in APP23 mice and whether they are increased by Am80/HX630 administration in vivo.

It is not clear whether Am80 and HX630 cross the blood brain barrier (BBB) and directly or indirectly affect the brain. It is known that Am580, an isomer of Am80, crosses the BBB in mice [17]. Am80 has been reported to attain some extent of access into the brain: cerebral tissue content of Am80 in normal male rats reaches around 100 pmol/g tissue at 2 h after subcutaneous administration of the drug at 1 mg/kg, then decreased at 6 h, and returned to the control levels at 24-120 h (76, 77). Rarβ is a target gene of RAR/RXR, and Rarβ mRNA was not increased by Am80/HX630 treatment in vivo (Supplementary FIG. 13A), in contrast to the in vitro study (FIG. 6). Because brain tissues were sampled at 1 day after last administration of the compounds, the concentration is considered not to be enough to increase Rarβ mRNA expression at the time point. The expression level of Rarβ mRNA may be tightly regulated (probably by a transcription factor), or the half-life of Rarβ mRNA may be short in vivo. On the other hand, the expression of Ide, another RAR/RXR-target gene, was increased by Am80/HX630 treatment in vivo as well as in vitro (FIGS. 3C, 4A). Moreover, mRNA for tPA, another target gene of RAR/RXR, was also increased by Am80/HX630 co-administration (Supplementary FIG. 13B). mRNA and protein of Cd36, a target gene of PPARγ/RXR, were increased by HX630 treatment both in vitro and in vivo (FIGS. 3A, 4A). These results suggest that Am80 and HX630 might cross the BBB and act directly in the brain.

Finally, we should mention that Goncalves et al. [17] recently reported that Am580 (an Am80 isomer with a reversed amide bond) ameliorated cognitive deficits (T-maze spontaneous alternation and Nest building tests) in Tg2576 mice, another AD model. Although the method of administration, kinds of behavioral experiments, and AD model were different from ours, we speculate that combined treatment with Am580 and an RXR ligand might also be synergistically more effective on memory deficits (MWM) in their model.

In conclusion, co-administration of Am80/HX630 effectively reduces insoluble Aβ peptides and improves cognitive deficits in APP23 mice. Combination treatment with RAR and RXR agonists, therefore, may be an effective approach for AD therapy.

INDUSTRIAL APPLICABILITY

The medicament of the present invention can be effectively used for therapeutic and/or preventive treatment of Alzheimer's disease.

CITATION LIST

Non Patent Literature

[NPL 1] Krstic D, Knuesel I (2013) Deciphering the mechanism underlying late-onset Alzheimer's disease. Nat Rev Neurol 9, 26-34.

[NPL 2] Vom Berg J, Prokop S, Miller K R, Obst J, Kälin R E, Lopategui-Cabezas I, Wegner A, Mair F, Schipke C G, Peters O, Winter Y, Becher B, Heppner F L (2012) Inhibition of IL-12/IL-23 signaling reduces Alzheimer's disease-like pathology and cognitive decline. Nat Med 18, 1812-1819.

[NPL 3] Heneka M T, Kummer M P, Stutz A, Delekate A, Schwartz S, Vieira-Saecker A, Griep A, Axt D, Remus A, Tzeng T C, Gelpi E, Halle A, Korte M, Latz E, Golenbock D T (2013) NLRP3 is activated in Alzheimer's disease and contributes to pathology in APP/PS1 mice. Nature 493, 674-678.

[NPL 4] Sporn M B, Roberts A B, Goodman D S, Gudas L J (1994) The retinoids: biology, chemistry, and medicine, 2nd ed. New York: Raven Press.

[NPL 5] Corcoran J P, So P L, Maden M (2004) Disruption of the retinoid signalling pathway causes a deposition of amyloid β in the adult rat brain. Eur J Neurosci 20, 896-902.

[NPL 6] Prinzen C, Müller U, Endres K, Fahrenholz F, Postina R (2005) Genomic structure and functional characterization of the human ADAM10 promoter. FASEB J 19, 1522-1524.

[NPL 7] Tippmann F, Hundt J, Schneider A, Endres K, Fahrenholz F (2009) Up-regulation of the α-secretase ADAM10 by retinoic acid receptors and acitretin. FASEB J 23, 1643-1654.

[NPL 8] Jarvis C I, Goncalves M B, Clarke E, Dogruel M, Kalindjian S B, Thomas S A, Maden M, Corcoran J P (2010) Retinoic acid receptor-α signalling antagonizes both intracellular and extracellular amyloid-β production and prevents neuronal cell death caused by amyloid-β. Eur J Neurosci 32, 1246-1255.

[NPL 9] Koryakina, A., Aeberhard, J., Kiefer, S., Hamburger, M. & Küenzi, P. (2009) Regulation of secretases by all-trans-retinoic acid. FEBS J., 276, 2645-2655.

[NPL 10] Lichtenthaler S F (2011) α-Secretase in Alzheimer's disease: molecular identity, regulation and therapeutic potential. J Neurochem 116, 10-21.

[NPL 11] Endres K, Fahrenholz F (2012) Regulation of α-secretase ADAM10 expression and activity. Exp Brain Res 217, 343-352.

[NPL 12] Goodman A B, Pardee A B (2003) Evidence for defective retinoid transport and function in late onset Alzheimer's disease. Proc Natl Acad Sci USA 100, 2901-2905.

[NPL 13] Shudo K, Kagechika H, Yamazaki N, Igarashi M, Takeda C (2004) A synthetic retinoid Am80 (tamibarotene) rescues the memory deficit caused by scopolamine in a passive avoidance paradigm. Biol Pharm Bull 27, 1.887-1889.

[NPL 14] Ding Y, Qiao A, Wang Z, Goodwin J S, Lee E S, Block M L, Allsbrook M, McDonald M P, Fan G H (2008) Retinoic acid attenuates β-amyloid deposition and rescues memory deficits in an Alzheimer's disease transgenic mouse model. J Neurosci 28, 11622-11634.

[NPL 15] Kawahara K, Nishi K. Suenobu M, Ohtsuka H, Maeda A, Nagatomo K, Kuniyasu A, Staufenbiel M, Nakagomi M, Shudo K, Nakayama H (2009) Oral administration of synthetic retinoid Am80 (Tamibarotene) decreases brain β-amyloid peptides in APP23 mice. Biol Pharm Bull 32, 1307-1309.

[NPL 16] Cramer P E, Cirrito J R, Wesson D W, Lee C Y, Karlo J C, Zinn A E, Casali B T, Restivo, J L, Goebel W D, James M J, Brunden K R, Wilson D A, Landreth G E (201.2) ApoE-directed therapeutics rapidly clear β-amyloid and reverse deficits in AD mouse models. Science 335, 1503-1506.

[NPL 17] Goncalves M B, Clarke E, Hobbs C, Malmqvist T, Deacon R, Jack J, Corcoran J P (2013) Amyloid β inhibits retinoic acid synthesis exacerbating Alzheimer disease pathology which can be attenuated by an retinoic acid receptor α agonist. Eur J Neurosci 37, 1182-1192.

[NPL 18] Fitz N F, Cronican A, Lefterov I, Koldamova R (2013) Comment on "ApoE-directed therapeutics rapidly clear β-amyloid and reverse deficits in AD mouse models". Science 340, 924-c.

[NFL 19] Price A R, Xu G, Siemienski Z B, Smithson L A, Borchelt D R, Golde T E, Felsenstein K M (2013) Comment on "ApoE-directed therapeutics rapidly clear β-amyloid and reverse deficits in AD mouse models". Science 340, 924-d.

[NPL 20] Tesseur I, Lo A C, Roberfroid A, Dietvorst S, Van Broeck B, Borgers M, Gijsen H, Moechars D, Mercken M, Kemp J, D'Hooge R, De Strooper B (2013) Comment on "ApoE-directed therapeutics rapidly clear β-amyloid and reverse deficits in AD mouse models". Science 340, 924-e.

[NPL 21] Veeraraghavalu K, Zhang C, Miller S, Hefendehl J K, Rajapaksha T W, Ulrich J, Jucker M, Holtzman D M, Tanzi R E, Vassar R, Sisodia S (2013) Comment on "ApoE-directed therapeutics rapidly clear β-amyloid and reverse deficits in AD mouse models". Science 340, 924-f.

[NPL 22] LaClair K D, Manaye K F, Lee D L, Allard J S, Savonenko A V, Troncoso J C, Wong P C (2013) Treatment with bexarotene, a compound that increases apolipoprotein-E, provides no cognitive benefit in mutant APP/PS1 mice. Mol Neurodegener 8, 18.

[NPL 23] Ross A C (2012) Vitamin A and retinoic acid in T cell-related immunity. Am J Clin Nutr 96, 1166S 11728.

[NPL 24] Iwata M, Eshima Y, Kagechika H (2003) Retinoic acids exert direct effects on T cells to suppress $T_h1$ development and enhance $T_h2$ development via retinoic acid receptors. Int Immunol 15, 1017-1025.

[NPL 25] Gadani S P, Cronk J C, Norris G T, Kipnis J (2012) IL-4 in the brain: a cytokine to remember. J Immunol 189, 4213-421.9.

[NPL 26] Derecki N C, Cardani A N, Yang C H, Quinnies K M, Crihfield A, Lynch K R, Kipnis J (2010) Regulation of learning and memory by meningeal immunity: a key role for IL-4. J Exp Med 207, 1067-1080.

[NPL 27] Delescluse C, Cavey M T, Martin B, Bernard B A, Reichert U, Maignan J, Darmon M, Shroot B (1991) Selective high affinity retinoic acid receptor alpha or beta-gamma ligands. Mol Pharmacol 40, 556-562.

[NPL 28] Amano Y, Noguchi M, Nakagomi M, Muratake H, Fukasawa H, Shudo K (2013) Design, synthesis and evaluation of retinoids with novel bulky hydrophobic partial structures. Bioorg Med Chem 21, 4342-4350.

[NPL 29] Ishida S, Shigemoto-Mogami Y, Kagechika H, Shudo K, Ozawa S, Sawada J, Ohno Y, Inoue K (2003) Clinically potential subclasses of retinoid synergists revealed by gene expression profiling. Mol Cancer Ther 2, 49-58.

[NPL 30] Nishimaki-Mogami T, Tamehiro N, Sato Y, Okuhira K, Sai K, Kagechika H, Shudo K, Abe-Dohmae 8, Yokoyama S, Ohno Y, Inoue K, Sawada J (2008) The RXR agonists PA024 and HX630 have different abilities to activate LXR/RXR and to induce ABCA1 expression in macrophage cell lines. Biochem Pharmacol 76, 1006-1013.

[NPL 31] Kagechika H, Kawachi E, Hashimoto Y, Shudo K (1984) New type inducers of differentiation of human HL-60 promyelocytic leukemia cells. Terephthalic anilides. Chem Pharm Bull 32, 4209-4212.

[NPL 32] Umemiya H, Fukasawa H, Ebisawa M, Eyrolles L, Kawachi E, Eisenmann G, Gronemeyer H, Hashimoto Y, Shudo K, Kagechika H (1997) Regulation of retinoidal actions by diazepinylbenzoic acids. Retinoid synergists which activate the RXR-RAR heterodimers. J Med Chem 40, 4222-4234.

[NPL 33] Sturchler-Pierrat C, Abramowski D, Duke M, Wiederhold K H, Mistl C, Rothacher S, Ledermann B, Bürki K, Frey P, Paganetti P A, Waridel C, Calhoun M E, Jucker M, Probst A, Staufenbiel M, Sommer B (1997) Two amyloid precursor protein transgenic mouse models with Alzheimer disease-like pathology. Proc Natl Acad Sci USA 94, 13287-13292.

[NPL 34] Shimizu E, Kawahara K, Kajizono M, Sawada M, Nakayama H (2008) IL-4-induced selective clearance of oligomeric β-amyloid peptide$_{1-42}$ by rat primary type 2 microglia. J Immunol 181, 6503-6513.

[NPL 35] Ohsawa K, Imai Y, Nakajima K, Kohsaka S (1997) Generation and characterization of a microglial cell line, MG5, derived from a p53-deficient mouse. Glia 21, 285-298.

[NPL 36] Dam D V, D'Hooge R, Staufenbiel M, Ginneken C V, Meir F V, De Deyn P (2003) Age-dependent cognitive decline in the APP23 model precedes amyloid deposition. Eur J Neuroeci 17, 388-396.

[NPL 37] Ishido M, Shudo K (2009) Oral administration of synthetic retinoid Am80 inhibits the development of type 1 diabetes in non-obese diabetic (NOD) mice. Biol Pharm Bull 32, 157-159.

[NPL 38] Morris R (1984) Developments of a water-maze procedure for studying spatial learning in the rat. J Neurosci Methods 11, 47-60.

[NPL 39] Vorhees C V, Williams M T (2006) Morris water maze: procedures for assessing spatial and related forms of learning and memory. Nat Protoc 1, 848-858.

[NPL 40] Iwata N, Takaki Y, Fukami S, Tsubuki S, Saido T C (2002) Region-specific reduction of Aβ-degrading endopeptidase, neprilysin, in mouse hippocampus upon aging. J Neurosci Res 70, 493-500.

[NPL 41] Huang S M, Mouri A, Kokubo H, Nakajima R, Suemoto T, Higuchi M, Staufenbiel M, Noda Y, Yamaguchi H, Nabeshima T, Saido T C, Iwata N (2006) Neprilysin-sensitive synapse-associated amyloid-β peptide oligomers impair neuronal plasticity and cognitive function. J Biol Chem 281, 17941-17951.

[NPL 42] Chomezynski P, Sacchi N (1987) Single-step method of RNA isolation by acid guanidinium thiocyanate-phenol-chloroform extraction. Anal Biochem 0.162, 156-159.

[NPL 43] Mildner A, Schlevogt B, Kierdorf K, Böttcher C, Erny D, Kummer M P, Quinn M, Brück W, Bechmann I, Heneka M T, Priller J, Prinz M (2011) Distinct and non-redundant roles of microglia and myeloid subsets in mouse models of Alzheimer's disease. J Neurosci 31, 11159-11171.

[NPL 44] Yamanaka M, Ishikawa T, Griep A. Axt D, Kummer M P, Heneka M T (2012) PPARγ/RXRα-induced and CD36-mediated microglial amyloid-β phagocytosis results in cognitive improvement in amyloid precursor protein/presenilin 1 mice. J Neurosci 32, 17321-17331.

[NPL 45] Tontonoz P, Nagy L, Alvarez J G, Thomazy V A, Evans R M (1998) PPARγ promotes monocyte/macrophage differentiation and uptake of oxidized LDL. Cell 93, 241-252.

[NPL 46] Heyman R A, Mangelsdorf D J, Dyck J A, Stein R B, Eichele G, Evans R M, Thaller C (1992) 9-cis Retinoic acid is a high affinity ligand for the retinoid X receptor. Cell 68, 397-406.

[NPL 47] Miwako I, Kagechika H (2007) Tamibarotene. Drugs Today 43, 563-568.

[NPL 48] Solomin L, Johansson C B, Zetterström R H, Biesonnette R P, Heyman R A, Olson L, Lendahl U, Frisén J, Perlmann T (1998) Retinoid-X receptor signalling in the developing spinal cord. Nature 395, 398-402.

[NPL 49] Zhang C, Hazarika P, Ni X, Weidner D A, Duvic M (2002) Induction of apoptosis by bexarotene in cutaneous T-cell lymphoma cells: relevance to mechanism of therapeutic action. Clin Cancer Res 8, 1234-1240.

[NPL 50] Kagechika H, Shudo K (2006) Synthetic retinoids: recent developments concerning structure and clinical utility. J Med Chem 48, 5875-5883.

[NPL 51] Oddo S, Caccamo A, Smith I F, Green K N, LaFerla F M (2006) A dynamic relationship between intracellular and extracellular pools of Aβ. Am J Pathol 168, 184-194.

[NPL 52] Tomiyama T, Matsuyama S, Iso H, Umeda T, Takuma H, Ohnishi K, Ishibashi K, Teraoka R, Sakama N, Yamashita T, Nishitsuji K, Ito K, Shimada H, Lambert M P, Klein W L, Mori H. (2010) A mouse model of amyloid β oligomers: their contribution to synaptic alteration, abnormal tau phosphorylation, glial activation, and neuronal loss in vivo. J Neurosci 30, 4845-4856.

[NPL 53] Melino G, Draoui M, Bernardini S, Bellincampi L, Reichert U, Cohen P (1996) Regulation by retinoic acid of insulin-degrading enzyme and of a related endoprotease in human neuroblastoma cell lines. Cell Growth Differ 7, 787.796.

[NPL 54] Bulloj A, Leal M C, Surace E I, Zhang X, Xu H, Ledesma M D, Castano E M, Morelli L (2008) Detergent resistant membrane-associated IDE in brain tissue and cultured cells: Relevance to Aβ and insulin degradation. Mol Neurodegener 3, 22.

[NPL 55] Killick R, Scales G, Leroy K, Causevic M, Hooper C, Irvine E, Choudhury A I, Drinkwater L, Kerr F, A1-Qassab H, Stephenson J, Yilmaz Z, Giese K P, Brion J P, Withers D J, Lovestone S (2009) Deletion of Irs2 reduces amyloid deposition and rescues behavioural deficits in APP transgenic mice. Biochem Biophys Res Commun 386, 257-262.

[NPL 56] Zhao Z, Xiang Z, Haroutunian V, Buxbaum J D, Stetka B, Pasinetti G M (2007) Insulin degrading enzyme activity selectively decreases in the hippocampal formation of cases at high risk to develop Alzheimer's disease. Neurobiol Aging 28, 824-830.

[NPL 57] Qiu W Q, Walsh D M, Ye Z, Vekrellis K, Zhang J, Podlisny M B, Rosner M R, Safavi A, Hersh L B, Selkoe D J (1998) Insulin-degrading enzyme regulates extracellular levels of amyloid 8-protein by degradation. J Biol Chem 273, 32730-32738.

[NPL 58] Maghsoodi B, Poon M, Nam C I, Aoto J, Ting P, Chen L (2008) Retinoic acid regulates RARα-mediated control of translation in dendritic RNA granules during homeostatic synaptic plasticity. Proc Natl Acad Sci USA 105, 1.6015-16020.

[NPL 59] Poon M, Chen L. (2008) Retinoic acid-gated sequence-specific translational control by RARα. Proc Natl Acad Sci USA 105, 20303-20308.

[NPL 60] Higuchi M, Iwata N, Matsuba Y, Takano J, Suemoto T, Maeda J, Ji B, Ono M, Staufenbiel M, Suhara T, Saido T C (2012) Mechanistic involvement of the calpain-calpastatin system in Alzheimer neuropathology. FASEB J 26, 1204-1217.

[NPL 61] Kalinin S, Richardson J C, Feinstein D L (2009) A PPARδ agonist reduces amyloid burden and brain inflammation in a transgenic mouse model of Alzheimer's disease. Curr Alzheimer Res 6, 431-437.

[NPL 62] Takeda N, Manabe I, Shindo T, Iwata H, Iimuro S, Kagechika H, Shudo K, Nagai R (2006) Synthetic retinoid Am80 reduces scavenger receptor expression and atherosclerosis in mice by inhibiting IL-6. Arterioscler Thromb Vase Biol 26, 1177-1183.

[NPL 63] Kawahara K, Suenobu M, Yoshida A, Koga K, Hyodo A, Ohtsuka H, Kuniyasu A, Tamamaki N, Sugimoto Y, Nakayama H (2012) Intracerebral microinjection of interleukin-4/interleukin-13 reduces β-amyloid accumulation in the ipsilateral side and improves cognitive deficits in young amyloid precursor protein 23 mice. Neuroscience 207, 243-260.

[NPL 64] Fenn A M, Henry C J, Huang Y, Dugan A, Godbout J P (2012) Lipopolysaccharide-induced interleukin (IL)-4 receptor-α expression and corresponding sensitivity to the M2 promoting effects of IL-4 are impaired in microglia of aged mice. Brain Behav Immun 26, 766-777.

[NPL 65] Nolan Y, Maher F O, Martin D S, Clarke R M, Brady M T, Bolton A E, Mills K H, Lynch M A (2005) Role of interleukin-4 in regulation of age-related inflammatory changes in the hippocampus. J Biol Chem 280, 9354-9362.

[NPL 66] Zhu B, Buttrick T, Bassil R, Zhu C, Olah M, Wu C, Xiao S, Orent W, Elyaman W, Khoury S J (2013) IL-4 and retinoic acid synergistically induce regulatory dendritic cells expressing Aldh1a2. J Immunol 191, 3139-3151.

[NPL 67] Carpentier A, Balitrand N, Rochette-Egly C, Shroot B, Degos L, Chomienne C (1997) Distinct sensitivity of neuroblastoma cells for retinoid receptor agonists: evidence for functional receptor heterodimers. Oncogene 15, 1805-1813.

[NPL 68] Leroy P, Nakshatri H, Chambon P (1991) Mouse retinoic acid receptor α2 isoform is transcribed from a promoter that contains a retinoic acid response element. Proc Natl Acad Sci USA 88, 10138-10142.

[NPL 69] Stellwagen D, Malenka R C (2006) Synaptic scaling mediated by glial TNF-α. Nature 440, 1054-1059.

[NPL 70] Chang E H, Savage M J, Flood D G, Thomas J M, Levy R B, Mahadomrongku I V, Shirao T, Aoki C, Huerta P T (2006) AMPA receptor downscaling at the onset of Alzheimer's disease pathology in double knockin mice. Proc Natl Acad Sci USA, 103, 3410-3415.

[NPL 71] Montgomery S L, Mastrangelo M A, Habib D, Narrow W C, Knowlden S A, Wright T W, Bowers W J (2011) Ablation of TNF-RI/RII expression in Alzheimer's disease mice leads to an unexpected enhancement of pathology: implications for chronic pan-TNF-α suppressive therapeutic strategies in the brain. Am J Pathol 179, 2053-2070.

[NPL 72] Dheen S T, Jun Y, Yan Z, Tay S, Ling E A (2005) Retinoic acid inhibits expression of TNF-α and iNOS in activated rat microglia. Glia 50, 21-31.

[NPL 73] Hellmann-Regen J, Kronenberg G, Uhlemann R, Freyer D, Endres M, Gertz K (2013) Accelerated degradation of retinoic acid by activated microglia. J Neuroimmunol 256, 1-6.

[NPL 74] Santello M, Volterra A (2012) TNFα in synaptic function: switching gears. Trends Neurosci 35, 638-647.

[NPL 75] Hickman S E, Allison E K, El Khoury J (2008) Microglial dysfunction and defective beta-amyloid clearance pathways in aging Alzheimer's disease mice. J Neorosci 28, 8364-8360.

[NPL 76] Mizojiri K, Okabe H, Sugeno K, Esumi Y, Takaichi M, Miyake T, Seki H, Inaba A (1997) Studies on the metabolism and disposition of the new retinoid 4-[(5,6,7,8-tetrahydro-5,6,8,8-tetra methyl-2-naphthyl)carbamoyl] benzoic acid. 1st communication: absorption, distribution, metabolism and excretion after topical application and subcutaneous administration in rats. Arzneimittelforschung, 47, 59-69.

[NPL 77] Liu X, Zhang Z, Jiang Y, Hu Y, Wang Z, Liu J, Feng R, Zhang J, Huang G (2014) Novel PEG-grafted nanostructured lipid carrier for systematic delivery of a poorly soluble anti-leukemia agent Tamibarotene: characterization and evaluation. Drug Deliv, in press

The invention claimed is:

1. A method for treating Alzheimer's disease comprising administering to a subject in need thereof a combination of a retinoic acid receptor (RAR) agonist and a retinoid X receptor (RXR) agonist, wherein the RAR agonist is selected from the group consisting of all trans retinoic acid, 4-{(5,6,7,8-tetrahydro5,5,8,8-tetramethyl-2-naphthalenyl)carbamoyl}benzoic acid, 4-{(5,6,7,8-tetrahydro5,5,8,8-tetramethyl-2-naphthalenyl)carboxamido}benzoic acid, 4-{(3,5-bistrimethylsilylphenyl)carbamoyl}benzoic acid, and 4-[(5,6,7,7a,8,9,10,11-octahydro-4H-2-benzo[ef]heptalenyl)carboxamido]benzoic acid, and wherein the RXR agonist is 4-[5H-2,3-(2,5dimethyl-2,5-hexano)-5-methyldibenzo[b,e]-diazepin-11-yl]benzoic acid or 6-[1-(3,5,5,8,8-pentamethyl-6,7dihydronaphthalen-2-yl)cyclopropyl]pyridine-3-carboxylic acid.

2. The method according to claim 1, wherein the RAR agonist is 4-{(5,6,7,8-tetrahydro5,5,8,8-tetramethyl-2-naphthalenyl)carbamoyl}benzoic acid.

3. The method according to claim 1, wherein the RXR agonist is 4-[5H-2,3-(2,5dimethyl-2,5-hexano)-5-methyldibenzo[b,e]diazepin-11-yl]benzoic acid.

4. The method according to claim 1, wherein the RAR agonist is 4-{(5,6,7,8-tetrahydro5,5,8,8-tetramethyl-2-naphthalenyl)carbamoyl}benzoic acid and the RXR agonist is 4-[5H-2,3-(2,5dimethyl-2,5-hexano)-5-methyldibenzo[b,e]diazepin-11-yl]benzoic acid.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggccatcca gagaatagaa                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
tttggagggt ctgacagtga                                                       20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcacactc cacaccaatg                                                       20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctgggttcc ttgtaggtca                                                       20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acggcttccc agaattacct                                                       20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcagcttggc aaggagagat                                                       20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taccaagggt ggcatctctc                                                       20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 8
agggcttctt tttcctctgc                                          20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttctttcccc ctatgctggg t                                        21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggagggctg ggtactatct c                                        21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgctcaatc catcgagaca c                                        21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttgtcctgg caaacgaagc                                          20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgaggcatc gtctccattc                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
acagatgctg tgaggtgcag                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctaaggccaa ccgtgaaaag                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accagaggca tacagggaca                                               20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggtccttac acatacagag ttcg                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggacttgcat gtaggaaatg tgga                                          24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagcctcagc cgaaactaca                                               20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 20
tttgtctcag catccatcca a                                              21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggccatcca gagaatagaa                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttggagggt ctgacagtga                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctaaggccaa ccgtgaaaag                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accagaggca tacagggaca                                                20

<210> SEQ ID NO 25
<211> LENGTH: 21
<212> TYPE: PRT
<213> ORGANISM: Mus sp.

<400> SEQUENCE: 25

Cys Asn Lys Glu His Lys Arg Pro Thr Gly Pro Pro Ala Lys Lys Ala
1               5                   10                  15

Ile Ser Glu Leu Pro
            20
```